United States Patent [19]

O'Brochta et al.

[11] Patent Number: 5,614,398
[45] Date of Patent: Mar. 25, 1997

[54] GENE TRANSFER SYSTEM FOR INSECTS

[75] Inventors: David O'Brochta, Columbia, Md.; William Warren, Whittlesea; Peter Atkinson, Canberra, both of Australia

[73] Assignee: The University of Maryland Biotechnology Institute, College Park, Md.

[21] Appl. No.: 344,695

[22] Filed: Nov. 18, 1994

[51] Int. Cl.⁶ .......................... C12N 15/63; C12N 15/85; C07H 21/04

[52] U.S. Cl. .................... 435/172.3; 435/320.1; 536/24.1; 514/44

[58] Field of Search ................ 435/69.1, 172.1, 435/172.3, 320.1; 536/23.1, 23.5, 24.1; 514/44

[56] References Cited

PUBLICATIONS

Marshall, "Gene Therapy's Growing Pains", Science, vol. 269, 25 Aug. 1995, pp. 1050–1055.

Primary Examiner—David Guzo
Attorney, Agent, or Firm—Oblon, Spivak, McClelland, Maier & Neustadt, P.C.

[57] ABSTRACT

DNA recombination can be effected through transposition by injecting a host with a transposition vector prepared from the terminal sequences of the Hermes element of *M. domestica* on either side of a structural gene to be expressed in the recombinant host. Transposition can be improved by use of a helper plasmid including the transposase gene of Hermes operably linked to a promoter sequence effective in the host.

6 Claims, 11 Drawing Sheets

TAATACCAACTGCAATGCAGTCTGTAT <CAGAGAACAACAACAAG— E1
AAAATGGATAATACGGCTTATCCGTAC <CAGAGAACAACAACAAG— E2
CATACGTTCAGGTACCGAACTGTGAAC <CAGAGAACAACAACAAG— E3
B5 —CTTGTTGAAGTTCTCTG> GTGGAGGGTATAAAAACACAGTTGAAA
B6 —CTTGTTGAAGTTCTCTC> AAATGATATATACTATATATCATTTGA

FIG.2

```
  1 CAGAGAACAACAACAAGTGGCTTATTTTGATACTTATGCGCCACTTGCTACTTATGAGTA  60
 61 CAATTGTGCTTTGCCACTTGAACAAAAAATTCATTGATTCATCGACACTCGGGTATGTTT 120
121 TGTCGTGTCGTTCTGCGCACTCAGTTAAATTTTTTGTCTTACTCTCTTGCTCTCAGCACA 180
181 TCAAGTGTTGTTACTTGTTGTTACTCAGTCGCCTGCCTTATGCTTTTGGAGAGCGAAAGC 240
241 ACAACGATCAGAACGGAGAAGTAACAACTTGTTTTGCTAACAAGTGGCTTATGCACTTGA 300
301 GTGTGTTTTACACATGTTTTTGAGTTTCACAGCAAAATGTTCCGATTTGAGCACAATAAT 360
361 TTTACCGTTATTTTGAGTTTTTTAGTTTTGAATAATAAATGTGATTTACTGTTCATCCTC 420
                 *  M Q K M D N L E V K A
421 AAAAGAGTTTAAGCAGTAGTAGAGATTAGATGCAGAAAATGGACAATTTGGAAGTGAAAG 480
      K I N Q G L Y K I T P R H K G T S F I W
481 CAAAAATCAACCAAGGATTATATAAAATTACTCCGCGACATAAAGGAACAAGTTTTATTT 540
      N V L A D I Q K E D D T L V E G W V F C
541 GGAACGTTTTAGCGGATATACAGAAAGAAGACGATACATTGGTGGAAGGGTGGGTGTTTT 600
      R K C E K V L K Y T T R Q T S N L C R H
601 GCCGAAAATGCGAAAAAGTTTTAAAATACACAACTAGGCAGACATCAAACTTATGTCGTC 660
      K C C A S L K Q S R E L K T V S A D C K
661 ATAAATGCTGTGCCTCTCTAAAGCAATCCCGAGAATTAAAAACTGTTTCAGCTGATTGCA 720
      K E A I E K C A Q W V V R D C R P F S A
721 AAAAGGAAGCAATTGAAAAATGTGCACAATGGGTGGTACGAGATTGTCGGCCTTTTTCGG 780
      V S G S G F I D M I K F F I K V G A E Y
781 CCGTCTCTGGATCCGGCTTTATCGATATGATAAAATTTTTTATTAAAGTTGGAGCCGAAT 840
      G E H V N E E L L P S I T L S R K V
841 ATGGTGAACATGTCAACGTTGAGGAATTGTTACCAAGTCCAATAACGCTATCGAGAAAGG 900
      T S D A K E K K A L I S R E I K S A V E
901 TAACTTCGGATGCAAAAGAAAAAAAAGCTCTGATTAGTCGAGAAATTAAGTCTGCTGTAG 960
      K D G A S A T I D L W T D N Y I K R N F
961 AGAAAGATGGTGCATCAGCAACGATAGATTTGTGGACCGATAATTATATAAAACGGAATT 1020
      L G V T L H Y H E N N E L R D L I L G L
1021 TTTGGGAGTAACGTTACACTACCATGAAAACAATGAACTGCGAGATCTAATTTTAGGTT 1080
      K S L D F E R S T A E N I Y K K L K A I
1081 TAAAGTCCTTAGATTTTGAAAGATCCACAGCAGAAAATATTTATAAGAAGCTTAAAGCCA 1140
```

FIG.3A

```
            F  L  Q  F  N  V  E  D  L  S  S  I  K  F  V  T  D  R  G  A
1141  TTTTTTTACAATTCAACGTCGAAGACTTGAGTAGTATAAAATTTGTGACAGATAGAGGAG  1200
            N  V  V  K  S  L  A  N  N  I  R  I  N  C  S  S  H  L  L  S
1201  CCAATGTCGTAAAATCATTGGCAAATAATATCAGAATTAACTGCAGCAGCCATTTGCTTT  1260
            N  V  L  E  N  S  F  E  E  T  P  E  L  N  V  P  I  L  A  C
1261  CAAACGTGTTGGAAAATTCATTTGAGGAGACACCTGAACTCAATGTGCCTATTCTTGCTT  1320
            K  N  I  V  K  Y  F  K  K  A  N  L  Q  H  R  L  R  S  S  L
1321  GCAAAAATATTGTAAAATATTTCAAGAAAGCCAATCTGCAGCACAGACTTCGAAGTTCTT  1380
            K  S  E  C  P  T  R  W  N  S  T  Y  T  M  L  R  S  I  L  D
1381  TAAAAAGTGAGTGCCCTACACGGTGGAATTCCACATACACGATGCTTCGATCTATTCTCG  1440
            N  W  E  S  V  I  Q  I  L  S  E  A  G  E  T  Q  R  I  V  H
1441  ACAACTGGGAAAGCGTGATTCAAATATTAAGTGAGGCGGGAGAGACACAGAGAATTGTTC  1500
            I  N  K  S  I  I  Q  T  M  V  N  I  L  D  G  F  E  R  I  F
1501  ATATAAATAAGTCGATAATTCAAACAATGGTCAACATCCTCGATGGGTTTGAAAGAATTT  1560
            K  E  L  Q  T  C  S  S  P  S  L  C  F  V  V  P  S  I  L  K
1561  TTAAAGAATTACAAACATGCAGTTCACCATCTCTGTGTTTTGTTGTGCCTTCCATTTTAA  1620
            V  K  E  I  C  S  P  D  V  G  D  V  A  D  I  A  K  L  K  V
1621  AAGTAAAAGAAATATGTTCACCTGACGTTGGCGACGTTGCAGATATAGCAAAATTGAAAG  1680
            N  I  I  K  N  V  R  I  I  W  E  E  N  L  S  I  W  H  Y  T
1681  TGAACATTATAAAAAATGTAAGAATAATATGGGAAGAAAATTTAAGCATATGGCACTACA  1740
            A  F  F  F  Y  P  P  A  L  H  M  Q  Q  E  K  V  A  Q  I  K
1741  CAGCATTTTTTTTCTATCCGCCCGCCTTGCATATGCAACAAGAGAAAGTGGCACAAATTA  1800
            E  F  C  L  S  K  M  E  D  L  E  L  I  N  R  M  S  S  F  N
1801  AAGAATTTTGCTTATCCAAAATGGAAGATTTGGAATTAATAAACCGCATGAGTTCCTTTA  1860
            E  L  S  A  T  Q  L  N  Q  S  D  S  N  S  H  N  S  I  D  L
1861  ACGAATTATCCGCAACTCAGCTTAACCAGTCGGACTCCAATAGCCACAACAGTATAGATT  1920
            T  S  H  S  K  D  I  S  T  T  S  F  F  F  P  Q  L  T  Q  N
1921  TAACATCCCATTCAAAAGACATTTCAACGACAAGTTTCTTTTTCCCGCAATTAACTCAGA  1980
            N  S  R  E  P  P  V  C  P  S  D  E  F  E  F  Y  R  K  E  I
1981  ACAATAGTCGTGAGCCACCAGTGTGTCCAAGCGATGAATTTGAATTTTATCGTAAAGAAA  2040
            V  I  L  S  E  D  F  K  V  M  E  W  W  N  L  N  S  K  K  Y
2041  TAGTTATTTTAAGCGAAGATTTTAAAGTTATGGAATGGTGGAATCTTAATTCAAAAAAGT  2100
            P  K  L  S  K  L  A  L  S  L  L  S  I  P  A  S  S  A  A  S
2101  ATCCTAAACTATCTAAACTGGCTTTGTCGTTATTATCAATACCTGCAAGTAGCGCTGCAT  2160
            E  R  T  F  S  L  A  G  N  I  I  T  E  K  R  N  R  I  G  Q
2161  CGGAAAGGACATTTTCCCTAGCTGGAAATATAATAACTGAAAAGAGAAACAGGATTGGGC  2220
            Q  T  V  D  S  L  L  F  L  N  S  F  Y  K  N  F  C  K  L  D
2221  AACAAACTGTCGACAGCTTGTTATTTTTAAATTCCTTTTACAAAAATTTTTGTAAATTAG  2280
```

FIG.3B

```
       I *
2281   ATATATAATTACATTTTTAAATAAAAAGAATATTTTTTATAAGTTTGTTTGTTAAAATAA   2340

2341   AAAAAAAAAATAAATAAATTTTGGACTGGAAAAAATTTAAGTTTAAAAGAAGCATTTTTC   2400
                 △                △

2401   TTTTTTTTTTTAATATACTTATGCTCTTTTCCTAGTCTTGTACAGAATCATATGCAATAC   2460
           △

2461   TACAAACAATAGCACACACACACAACCCTCATGTTCAATGAGTATACAACACAACAAGAA   2520

2521   GTGAGTATAATTTGCCAATTGACAAATCGCACACGTCCACTTGTGAGTTTGTACACTTTT   2580

2581   TACTCTCTCATACTCTAGCGGTGATCTTAACATCAAACAACTGTTGTTGTTAAGTTGTGA   2640

2641   AAAAATACTCGTGTATAAAAAAATACTTGCACTCAAAAGGCTTGACACCCAAAACACTTG   2700

2701   TGCTTATCTATGTGGCTTACGTTTGCCTGTGGCTTGTTGAAGTTCTCTG               2749
                                       ^^^_←――――――――――――――――――――=
```

FIG.3C

```
   1 cagagaacaa caacaagtgg cttatttga tacttatgcg ccacttgcta
  51 cttatgagta caattgtgct ttgccacttg aacaaaaaat tcattgattc
 101 atcgacactc gggtatgttt tgtcgtgtcg ttctgcgcac tcagttaaat
 151 tttttgtctt actctcttgc tctcagcaca tcaagtgttg ttacttgttg
 201 ttactcagtc gcctgccta tgcttttgga gagcgaaagc acaacgatca 251 gaacggagaa gtaacaactt gttttgctaa caagtggctt atgcacttga
 301 gtgtgttta cacatgtttt tgagtttcac agcaaaatgt tccgatttga
 351 gcacaataat tttaccgtta tttgagttt tttagttttg aataataaat
 401 gtgatttact gttcatcctc aaaagagttt aagcagtagt agagattaga
 451 tgcagaaaat ggacaatttg gaagtgaaag caaaaatcaa ccaaggatta 501 tataaaatta ctccgcgaca taaagaaca agtttattt ggaacgtttt
 551 agcggatata cagaagaag acgatacatt ggtggaagg tgggtgtttt
 601 gccgaaaatg cgaaaaagtt ttaaaataca caactaggca gacatcaaac
 651 ttatgtcgtc ataaatgctg tgcctctcta agcaatccc gagaattaaa
 701 aactgtttca gctgattgca aaaaggaagc aattgaaaaa tgtgcacaat 751 gggtggtacg agattgtcgg ccttttttcgg ccgtctctgg atccggcttt
 801 atcgatatga taaaattttt tattaaagtt ggagccgaat atggtgaaca
 851 tgtcaacgtt gaggaattgt taccaagtcc aataacgcta tcgagaaagg
 901 taacttcgga tgcaaaagaa aaaaagctc tgattagtcg agaaattaag
 951 tctgctgtag agaaagatgg tgcatcagca acgatagatt tgtggaccga 1001 taattatata aaacggaatt ttttgggagt aacgttacac taccatgaaa
1051 acaatgaact gcgagatcta atttaggtt taaagtcctt agatttgaa
1101 agatcccacag cagaaaatat ttataagaag cttaaagcca tttttaca
1151 attcaacgtc gaagacttga gtagtataaa atttgtgaca gatagaggag
1201 ccaatgtcgt aaaatcattg gcaaataata tcagaattaa ctgcagcagc
```

```
1251 catttgcttt caaacgtgtt ggaaaattca tttgaggaga cacctgaact
1301 caatgtgcct atttcttgctt gcaaaaatat tgtaaaatat ttcaagaaag
1351 ccaatctgca gcacagactt cgaagttctt taaaaagtga gtgccctaca
1401 cggtggaatt ccacatacac gatgcttcga tctattctcg acaactggga
1451 aagcgtgatt caaatattaa gtgaggcggg agagacacag agaattgttc 1501 atataaataa gtcgataatt caaacaatgg tcaacatcct cgatggtttt
1551 gaaagaattt ttaaagaatt acaaacatgc agttcaccat ctctgtgttt
1601 tgttgtgcct tccattttaa aagtaaaaga atatgttca cctgacgttg
1651 gcgacgttgc agatatagca aaattgaaag tgaacattat aaaaaatgta 1701 agaataatat gggaagaaaa tttaagcata tggcactaca cagcattttt 1751 tttctatccg cccgccttgc atatgcaaca agagaaagtg gcacaaatta
1801 aagaattttg cttatccaaa atggaagatt tggaattaat aaaccgcatg
1851 agttcctta acgaattatc cgcaactcag cttaaccagt cggactccaa
1901 tagccacaac agtatagatt taacatccca ttcaaaagac atttcaacga
1951 caagtttctt tttcccgcaa ttaactcaga acaatagtcg tgagccacca 2001 gtgtgtccaa gcgatgaatt tgaattttat cgtaaagaaa tagttatttt
2051 aagcgaagat tttaagtta tggaatggtg gaatcttaat tcaaaaaagt
2101 atcctaaact atctaaactg gctttgtcgt tattatcaat acctgcaagt
2151 agcgctgcat cggaaaggac atttcccta gctggaaata taataactga
2201 aaagagaaac aggattgggc aacaaactgt cgacagcttg ttatttttaa
```

FIG. 5C

```
2251 attccttta caaaattt tgtaaattag atatataatt acatttttaa
2301 ataaaagaa tatttttat aagtttgttt gttaaataa aaaaaaaaa
2351 taaataaatt ttggactgga aaaaattaa gtttaaaga agcatttttc
2401 tttttttt taatatactt atgctctttt cctagtcttg tacagaatca
2451 tatgcaatac tacaaacaat agcacacaca cacaaccctc atgttcaatg 2501 agtatacaac acaacaagaa gtgagtataa tttgccaatt gacaaatcgc
2551 acacgtccac ttgtgagttt gtacactttt tactctctca tactctagcg
2601 gtgatcttaa catcaaacaa ctgttgttgt taagttgtga aaaatactc
2651 gtgtataaaa aaatacttgc actcaaaagg cttgacaccc aaaacacttg
2701 tgcttatcta tgtggcttac gtttgcctgt ggcttgttga agttctctg
```

GENE TRANSFER SYSTEM FOR INSECTS

The United States government may have rights in this application by reason of government contract NIH 03-5-20014.

FIELD OF THE INVENTION

This invention pertains to a system for achieving transpositional recombination of DNA in insect cells and insects and other organisms. Specifically, heterologous DNA, terminated at both ends with the terminal inverted repeat sequences of the 2749 base pair Hermes element of the housefly, *M. domestica,* when injected into a host is recombined through transposition in the host, which may be other than *M. domestica.* Transposition may be aided by a helper plasmid comprised of a promoter sequence operably linked to the DNA encoding the transposase protein of the Hermes element.

BACKGROUND OF THE INVENTION

A variety of transposable genetic elements have been identified. A well studied insect transposable element, P, O'Brochta et al., mobility of P elements in drosopholids and nondrosopholids, NPAS 85,6052–6056 (1988) has, despite substantial study, failed to provide a mechanism for affecting recombination outside of drosophila. Other transposable elements, including hobo isolated from *T. melanogaster,* Ac from *Zea mays* and Tam 3 from antirrhinum majus have all been identified as having common elements. Calvi et al., *Cell* 66, p. 465–471 (1991). These are constituent members of a family of transposase members which are identified by terminal inverted repeat sequences sandwiching a sequence encoding a transposase protein in a single open reading frame (ORF), the protein generally consisting of three identifiable domains. This family is identified as a family of transposable elements or hAT elements.

The preparation of transgenic, recombinant insect cell lines and insects continues to be an object of substantial commercial interest. The preparation of biological control agents capable of passing a dominant lethal genotype to a wild population, or infertile mating competitors, is currently effected through the use of blind chemical or irradiation mutagens. Tools for preparing effective recombinant individuals selected for a specific genotype would greatly improve these modalities.

Additionally, genetic analysis, protein assays and the like are all capable of making use of such tools. Additionally, insect cell lines are currently used for the expression of foreign proteins. The proteins expressed in these insect cell systems can have a variety of uses. Currently, most insect cell expressions systems are transient (as opposed to continuous) and based on baculovirus infection. Continuous expression systems are advantageous.

Further, altering genotypes by the introduction of an exogenous gene is widely applicable technology. Gene therapy relies on just such a process. Transgenic technology is also being developed for animals for the purposes of improved livestock, poultry or aquaculture production. Thus, the provision of an effective system for achieving recombination of exogenous material into a host for expression of the same continues to be an object of those of skill in the art.

SUMMARY OF THE INVENTION

A method has been developed which will permit the genetic engineering of insects and insect cells of biomedical, agricultural and commercial importance. The method enables the user to introduce DNA into the chromosomes of insects, insect cells and other potential hosts. Once integrated, the DNA is contiguous with the existing chromosomes and will be inherited with the chromosomes. A transposable element has been identified in the housefly, *Musca domestica.* The transposable element is called Hermes. Hermes is 2790 base pairs in length. The terminal sequences play an important role in transposition, while the central element encodes for a protein (transposase) which assists in the movement of Hermes. Excising the transposase protein encoding sequence, and substituting a piece of foreign DNA between the terminal sequences provides a transposable element. The tranposase gene is inserted separately on a plasmid and placed under the regulatory control of a standard promoter, such as the Drosophila heat shock-70 promoter. This binary gene transformation system consisting of a vector which comprises the terminal sequences of Hermes sandwiching the heterologous DNA and a helper plasmid, which produces the tranposase protein to mediate transposition, effectively achieves recombination through transposition.

BRIEF DESCRIPTION OF THE DRAWINGS

FIG. 2. The termini of Hermes were identified by the alignment of sequences obtained from independent elements. DNA sequences of the three left termini (E1 (SEQ ID NO:3), E2 (SEQ ID NO: 4), and E3 (SEQ ID NO:5) and two right termini (B5 SEQ ID NO:6) and B6 (SEQ ID NO:7), including 27 bp of flanking genomic sequences, are given in the 5' to 3' orientation. The 17 bp inverted terminal repeats of each Hermes element are indicated by solid arrows.

FIG. 3. Consensus Hermes nucleotide sequence (SEQ ID NO:1), including translation (SEQ ID NO:2) of the transposase coding region. Terminal inverted repeat sequences are double underlined, nucleotides differing between independent Hermes elements are triple underlined, nucleotide deletions indicated by capital deltas, stop codons by an asterisk (*) and the suberminal pentanucleotide motif conserved between Hermes and hobo marked with carets (^). amino acid residues encoded by ORF1 are shown above the DNA sequence.

FIG. 5. Linear Hermes nucleotide sequence (SEQ ID NO:1) without characteristics.

FIG. 6 (Parts A and B). Amino acid sequence alignments of the putative DNA binding regions (A SEQ ID NOS:8–12)

Figure 1:
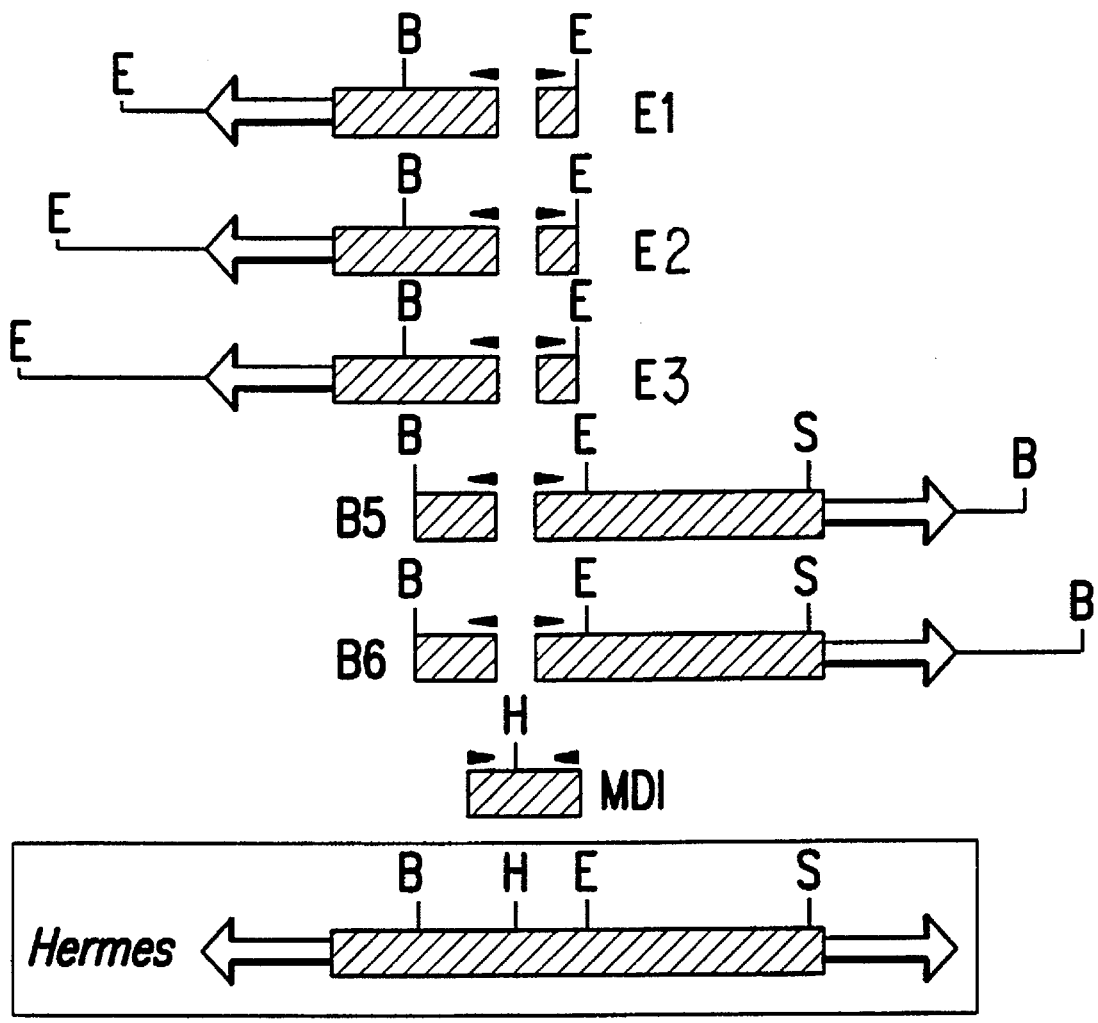
FIG. 1 Summary of independent Hermes sequences obtained from PCR and inverse PCR and used in the construction of a consensus full length Hermes element. Cones labelled E1 (SEQ ID NO:3), E2 (SEQ ID NO:4) and E3 (SEQ ID NO:5) were obtained from inverse PCR amplication of EcoRI circles, B5 and B6 from inverse PCR amplification of BamHI circles and MDI from degenerate PCR as described in Atkinson et al (1993). Shaded boxes indicate transposase coding sequences, open boxes flanking Hermes sequences, open triangles inverted terminal repeats and thin horizontal lines flanking *M. domestica* genomic DNA sequences. The location of PCR primers are indicated by arrowheads. Restriction sites: E, EcoRI; B, BamHI; H, HindIII; S, SalI.

and highly conserved C-terminal sequences (B SEQ ID NOS:13–19) of various hAT element transposases. Identical residues are indicated by white letters on a black background and chemically similar residues as black letters on a shaded background. The solid black rectangle indicates residues found to be essential for Ac transposase DNA binding and the U-shaped arrows indicate the pairs of charged resides that when substituted for alanine (A), or for glutamine (Q), abolish DNA binding (Feldmar and Kunze 1991).

Figure 7:
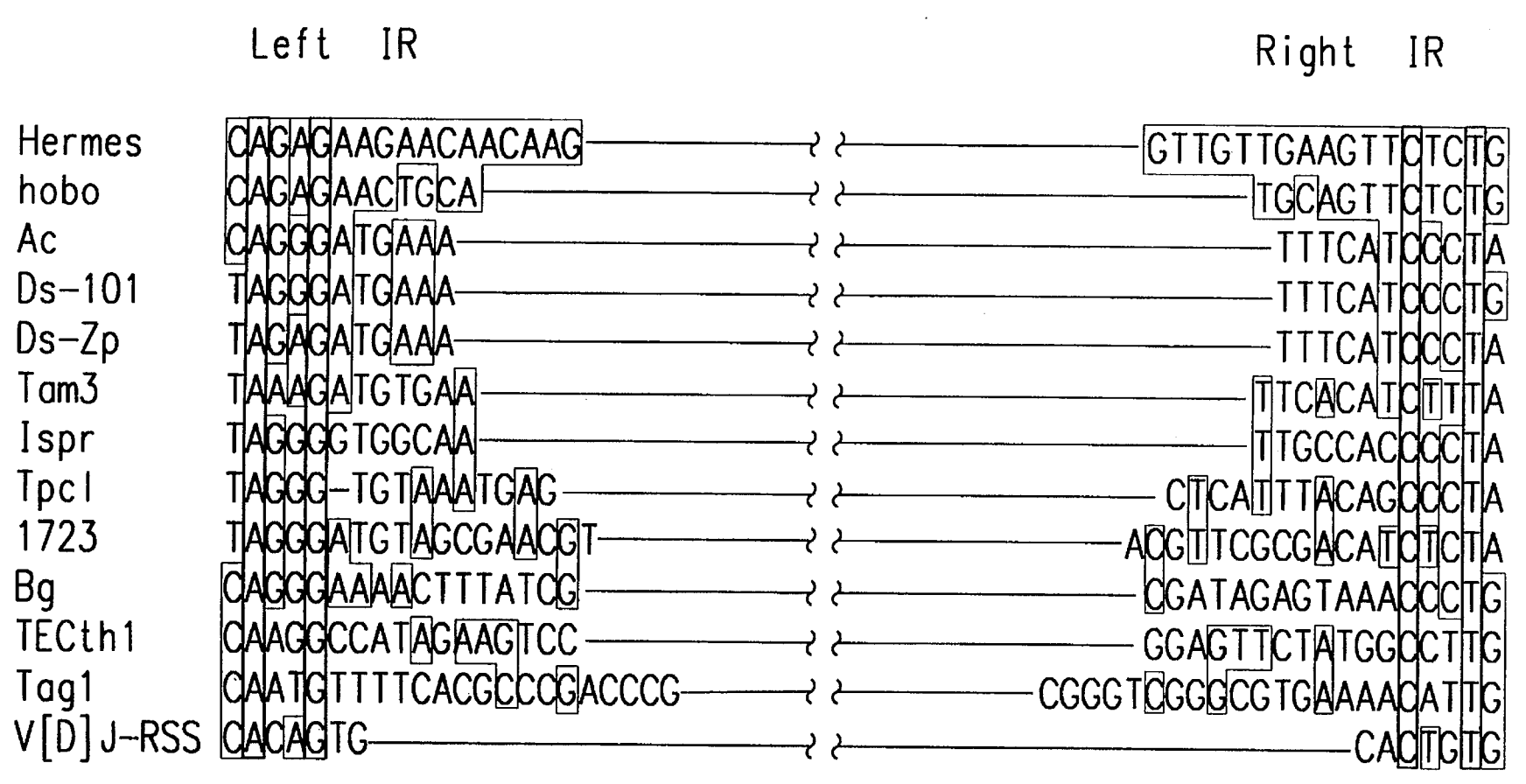

FIG. 7. Nucleotide sequences (SEQ ID NOS:20–43) of the left and right terminal inverted repeats (IRs) of members the hAT element family and other related elements. Bases identical in all elements are shown as white letters on a black background and those identical to the Hermes elements are shown by black letters on a shaded background. A gap in the Tpc1 sequence was introduced only to preserve the inverted repeat. Data presented here were obtained from the following EMBL database entries or papers: Hermes(*M. domestica*) this paper; hobo (*D. melanogaster*), M69216; Ac(*Z. mays*), X05424 and X05425; Ds-101 (*Z. mays*), X07147; Ds-Zp (*Z. perennis*), X54710; Tam3 (*A. majus*), X55078; Ipsr(p. sativum), Bhattacharyysa et al., (1990); Tpc1 (*P. crispum*), Herrmann et al., (1988); 1723 (*X. laevis*) X00079 and X00077, Bg(*Z. mays*), X56877; Tag1(*A. thaliana*), L12220; TECth1 (*C. thummi*), X17627; V[D]J-RSS, (Hesse et al., 1989).

DETAILED DESCRIPTION OF THE INVENTION

The Hermes element nucleotide sequence (SEQ ID NO:1) is set forth in FIG. 5. In FIG. 3, the sequence is broken down to identify the terminal inverted repeater sequences (SEQ ID NO:20–21), which are essential for the transposition vector, as well as the central transposase (SEQ ID NO:2) encoding region. Also noted are nucleotide identities which are questionable by reason of the PCR identification of a variety of fragments overlapping or deleting the identified sequences. Nonetheless, the full sequence pictured in FIG. 5 (SEQ ID NO:1) is the Hermes element.

The Hermes element provides a system for effecting tranpositional recombination. The system comprises the use of two separate elements. The transposition vector is comprised of terminal sequences drawn from the Hermes terminal inverted repeater sequences, and additional base pairs of desired length, in sequence, sandwiching the heterologous DNA desired to be inserted into the host cell. If the host cell contains and expresses a tranposase protein, which are widely variable and highly conserved, simple injection of the transpositional vector will affect transposition of the heterologous DNA, with subsequent generations expressing that DNA. In the event the host is of a sufficiently different species to render the transposase present insufficient to aid transposition, or in the even the host lacks a transposase protein expressed, transposition can be improved by use of a "helper plasmid" which comprises the transposase (SEQ ID NO:2) encoding sequence identified in FIG. 3 operably linked to a suitable promoter plasmid, such as the Drosophila heat shock-70 promoter. Thus, the minimum required for tranpositional recombination in this system is a vector comprising the 17 base pair terminal $3^1$ sequence and 17 base pair terminal $5^1$ sequence (terminal inverted repeater sequences) identified by underlining in FIG. 3 (SEQ ID NOS:20–21) sandwiching the heterologous structural gene encoding the protein whose expression is desired. Alternatively, these terminal sequences may sandwich a genotype carrying a lethal dominant whose expression is not desired immediately, but will be distributed to generations in the wild and progeny.

The terminal sequences of the transposition vector need not be limited to the 17 base pair sequences identified. Larger sequences, up to and including the full 434 base pair sequence set forth in FIG. 3 preceding the stop codons prior to and at the end of the structural region may be used as the terminal ends of the transpositional vector.

As noted, transposition may be aided by the use of a "helper plasmid" which comprises the transposase nucleotide sequence set forth in FIG. 3 operably linked to a suitable promoter sequence. Although the Drosophila heat shock-70 promoter sequence is expressly used herein, other promoter sequences suitable for the particular host cell will be known to those of skill in the art and can be used according to established methodologies. The host or target cell need not be an insect cell, although the same is obviously preferred from the point of view of genetic relationship. Nonetheless, the vector is species independent, and maybe used to effect recombination through transposition in non-insectile species, including mammals and humans, thus, the gene transport system of the claimed invention provides a method for introducing heterologous DNA not only into other insects and insect cell lines, but other organisms as well. A principle, realized goal discussed below, is the transformation of insects through recombination.

The validity of this concept is demonstrated by the results of two experiments.

a. Demonstration of Hermes' ability to transpose in the host insect, *Musca domestica*

The ability of Hermes to transpose was tested using modifications of a method developed by us and described in the attached reprint. Instead of a hobo element as described in the attached report, we used a Hermes element and a helper plasmid encoding Hermes transposase. Using this assay, we recovered Hermes transposition events into a target plasmid.

b. Demonstration of Hermes' ability to transpose in a divergent insect, *D. melanogaster*

We constructed a non-autonomous Hermes transposable element containing a dominant genetic marker (the wild-type allele of the white gene) flanked by the terminal sequence of the Hermes element. This marked element and the Hermes transposase—encoding plasmid were injected into the pole region of preblastoderm *D. melanogaster* embryos. Injection and identification of transgenic animals relied on established methods. Transgenic *D. melanogaster* were subsequently recovered. *D. melanogaster* and *M. domestics* are distantly related with a common ancestor 150 million years ago.

Variations and Alternate Form

Variations and alternate forms that are within the scope of this invention would include variations and alternate means of expressing Hermes transposase, alternate "marker genes" located between the terminal sequences of Hermes for the purposes of identifying the transgenic animal and animal cell, and variations in the length and sequence composition of the Hermes terminal sequences used in the vector. Variations in the sequence of the terminal sequences of Hermes could result in either increased or decreased ability of the element to act as a vector.

Novel Features a. The novel feature of this invention is the transposable element upon which the vector and "helper plasmids"

are derived. The Hermes transposable element is a newly discovered element and is different from any of the transposable elements currently employed as gene vectors.

b. The greatest deficiency in current insect transgenesis technology is its limited applicability. Insect transgenesis technology is available only for insects in the genus Drosophila. The invention described here, eliminates this barrier and makes insect transgenesis technology available for a wide range of insects and other hosts.

Application of this technology.

a. Applications related to insects:

1. Genotype manipulation

This technology will be used to manipulate the genotypes of insects. Genotype manipulation is currently used to control insect pest populations. For example, high rates of dominant lethal mutations are induced in mass reared populations either chemically or with radiation. These artificially bred and mutated insects are released into a wild population of the same species, where they either disseminate these deleterious mutations resulting in population decline, or they mate with "wild" insects, but produce no offspring thereby disrupting the pest's reproductive cycle.

In a very limited number of examples, the genotype of certain predacious mites has been altered by conventional breeding methods to confer insecticide resistance. These insecticide resistant mites are used as biocontrol agents in Integrated Pest Management Programs.

Insect genotype manipulation will become more widely available as a result of our invention leading to new ways of producing and employing genotype-altered arthropods. Hence, this invention will result in the production of new and more effective biocontrol agents.

Genome analysis

Transposable elements like the Hermes element are very useful in a number of aspects of genome analysis. For example, Hermes will be used as a means of identifying and isolating genes using established transposase tagging and enhancer trapping strategies. Hence, Hermes will be developed in various forms as a genome analysis tool. These tools will be useful to those investigating a wide variety of insects.

Applications unrelated to Insects.

Altering genotypes by the introduction of an exogenous gene is a widely applicable technology. Transgenic technology is being developed for animals for the purposes of improved livestock, poultry, or aquaculture production. Transgenic technology is also being used as a therapy for human diseases. This invention could provide new and more efficient means of creating transgenic animals other than insects.

EXAMPLES

Isolation of hobo Transposase-Like Sequences from *M. domestica*.

To determine whether *M. domestica* possessed sequences which might encode transposase-like protein, degenerate oligonucleotides similar to regions previously identified by Calvi et al. as being conserved between hobo, Ac, and Tam3 were used as primers in a PCR with *M. domestica* genomic DNA as template. These primers were capable of amplifying the predicted 454-bp hobo fragment with a hobo-containing Oregon-R strain of D-melanogaster, and a similarly sized fragment was amplified from the genome of a Maryland strain of *M. domestica*. This fragment was cloned and the DNA sequence of a single recombinant clone was determined and found to be 453 bp long. When the sequence found between the PCR primers in this clone was aligned with the corresponding region of the HFL1 hobo element, the two sequences were found to share 61% nucleotide identity. The insertion of 1-bp gap was necessary to optimally align the sequence, conceptual translation of which yielded a single continuous open reading frame that shares 61% amino acid identity and 76% amino acid similarity with the putative HFL1 transposase.

Genomic DNA was prepared from two strains of *M. domestica* of different geographic origins, digested with a number of restriction enzymes, and analyzed for the presence of sequences homologous to the cloned PCR product by Southern blot methodology. Strains analyzed originated from wild populations in Maryland and Florida and had been maintained in laboratory culture for over 10 years.

(i) *M. domestica* genomic DNA

The Maryland and Mullinix strains were obtained from the USDA Livestock Insect Laboratory, Beltsville, Md. and the Florida strain was obtained from the USDA South Atlantic Area Medical and Veterinary Entomology Laboratory. All other strains were obtained from the Department of Entomology, Texas A & M University. All strains examined were derived from wild caught flies with the exception of Sbo, which is a multiply marked laboratory strain carrying the stubby, brown body and ocra eye mutations. Genomic DNA was prepared whether from embryos as described by Miklos (1984) or from single adults by a modification of the method of Lifton (Bender, Spierer & gogness, 1983).

(ii) PCR analysis of strains

The oligonucleotide primers, 5'-TTGTTGTTACT-CAGTCGC-3' (SEQ ID NO:44) and 5'-GTTTGATGTTAA-GATCACC-3' were used to amplify Hermes sequences from genomic DNA prepared from single adult *M. domestica* of various strains. Each PCR reaction contained 50 mM-KCl, 10mM Tris-HCl (pH 8.3), 1.8 mM-$MgCl_2$, 0.125 μm dNTPs, 0.2 μm of each primer, 12% sucrose, 0.2 mM cresol red, 200 ng of template DNA and 2.2 units of Taq polymerase (AmpliTaq, Perkin-Elmer) in a total volume of 50 μl. PCR amplification was performed in a Perkin-Elmer 9600 thermocycler programmed for 95° C. (3 min) then 35 cycles of 50° C. (30 s), 72° C. (2.5 min) and 95° C (20s) followed by 10 min at 72° C. Amplified products were then size fractionated by electrophoresis in 1.2% agarose and visualized by fluorescence in ethidium bromide.

(iii) Inverse PCR

20 μg of genomic DNA, purified from embryos of the Maryland strain of *M. domestica*, was digested to completion with EcoRI or BamHO (New England Biolabs) in accordance with the supplier's recommendations. After electrophoresis through 0.8% agarose the 2 to 3 kb and 3 to 5 kb fractions of each digest were excised from the gel and purified by NaI/glass-milk (Gene-Clean, BIO101 Inc). Circularization of the DNA in each fraction was performed at a DNA concentration of 0.5 μg/ml in 30 mM TrisHC; pH 7.8, 10 mM-$MgCl_2$, 10 mM dithiothreitol, 5 mMATP and 1600 units/ml T4 DNA ligase (New England Biolabs) for 18 at 12° C. Ligated DNA was recovered by NaI/glass-milk purification and digested with HindIII (New England Biolabs) to linearize Hermes containing molecules. Approximately 150 ng of this DNA was used 100 μl PCR.

PCR amplifications contained 50mM-KCl, 10 mM Tris-HCl (Ph 8/3), 2 mM-MgCl$_2$, 200 μM dNTPs, one was bead (AmpliWax, Perkin-Elmer), template DNA and 0.1 μM of each primer, Amplifications of EcoRIligated molecules were performed with Primer 1 (5'-CTGTGGATCTTTCAAAAT AAGG-3'(SEQ ID NO:46)) and Primer 4 (5'-GAGACAC-CTGAACTCAATGTGC-3'(SEQ ID NO:47) whereas in those performed on BamHI ligated molecules used Primer 4 and Primer 5 (5'-CGCAGTTCATTGTTTTCATGG-3'(SEQ ID NO:48)). Amplifications were initiated by the addition of 3 units Taq polymerase and performed as follows: two cycles of 95° C. (60 s), 58° C. (15 s), 72° C. (5 min), 35 cycles of 95° C. (15 s), 58° C. (15s), 72° C. (3 min) followed by 10 min at 72° C. Amplified products were size fractionated by electrophoresis in 1% agarose, gel purified and cloned as blunt-ended fragments into the pBCKS(+) vector (Stratagene).

(iv) DNA sequence determination and analysis

DNA sequencing was performed by the chain termination method of Sanger, Nickel & Coulsen (1977) using modified T7 DNA polymerase (Sequenase, United States Biochemical) under conditions recommended by the supplier. Full DNA sequences of the cloned PCR products was obtained with the aid of exonuclease III generated deletions (Henikoff, 1987) as well as with Hermes specific oligonucleotide sequencing primers. DNA sequences analyses were performed using version 7.1 of the GCG package of programs (Deveraux, Haeberli & Smithies, 1984) and nucleic acid sequence database searches were performed using the BLAST algorithm (Altschul et al. 1990) using the electronic-mail search facility provided by the National Center for Biotechnology Information (NCBI).

(i) Hermes sequence and structure

Inverse PCR, a variation of the polymerase chain reaction that permits the amplification of regions of unknown sequence that flank a known sequence (Ochman, Gerber & Hartl, 1988; Triglia, Peterson & Kemp 1988), was used to amplify and isolate overlapping segments of several Hermes elements from the Maryland strain of *M. domestica*. Initially, genomic DNA was digested with EcoRI, the resulting fragments circularized and those containing Hermes sequences amplifies using PCR with oligonucleotide primers based upon the sequence data presented in Atkinson, Warren & O'Brochta (1993). Prior to circularization the template DNA was size-fractionated to bias the PCR towards amplification of full length Hermes sequences. In this way DNAs from three independent Hermes elements (denoted E1, E2 and E3) were isolated, cloned and sequenced. These clones contain sequences between an internal EcoRI site located within the Hermes transposes encoding region and the next EcoRI site in the upstream flanking genomic DNA (FIG. 1). The left terminus of Hermes was identified by aligning these three elements, which are collinear until approximately 1.4 kb upstream of the EcoRI site, at which point their identity abruptly ends (FIG. 2). The 3'Hermes sequences, including the C-terminal transposes encoding region and the sequences that comprise the right end of Hermes, were isolated by inverse PCR from BamHI digested genomic DNA. DNAs from two independent Hermes elements (denoted B5 and B6), spanning the region from an internal BamHI site within the N-terminal region of the Hermes transposase to the next BamHI site in the downstream flanking genomic DNA (FIG. 1), were amplified, clones and sequenced. The right terminus of Hermes was identified by aligning the B5 and B6 sequences and observing the point where their identities end (FIG. 2).

Alignment of the overlapping regions from the E1 (SEQ ID NO:3), E2, E3, B5 and B6 sequences yielded a full length consensus Hermes element sequence of 2749 bp (FIG. 3). These data were generated by compiling the sequences of several independent recombinants of each inverse PCR generated product, as well as three additional recombinants (denoted MD1 in FIG. 1) carrying the PCR product whose sequence was reported in Atkinson, Warren & O'Brochta (1993). In this way sequence variation introduced during amplification by Taq polymerase was distinguished from naturally occurring sequence variation between elements. In general, Hermes elements are quite homogeneous in sequence. Very low levels of nucleotide polymorphism were found between the different Hermes elements sequenced and although several single base deletions were observed there were no large DNA insertions or deletions (FIG. 3).

(ii) Hermes sequence variation between *M. domestica* strains

Figure 4:
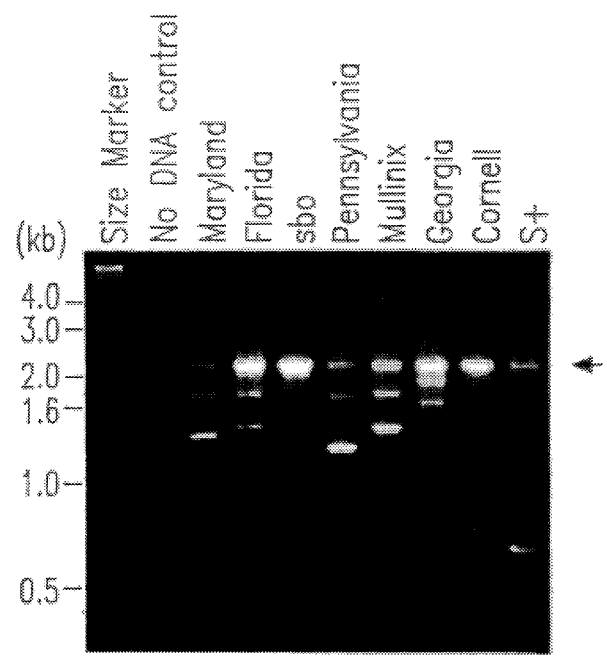
FIG. 4. Ethidium bromide stained agarose gel containing Hermes sequences amplified by PCR from genomic DNA extracted from single *M. domestica* of various strains. Size standards are shown left most and an arrow at right indicates the 2.4kb PCR product derived from full length Hermes elements.

Oligonucleotide primers specific to subterminal Hermes sequences were used in a PCR reaction to investigate the sequence length heterogeneity of Hermes elements against *M. domestica* strains. These oligonucleotides, whose 5' bases end at positions 195 and 2618 (FIG. 3), were used to amplify internal Hermes sequences from genomic DNA extracted from single flies of various strains. As shown in FIG. 4, the largest band amplified were these primers is 2.4 kb. The size of this amplification product is consistent with the data presented in FIG. 3, which predict that these primers would generate a 2424 bp product from a full-length Hermes element. All strains examined contain a 2.4 kb band, indicating that all contain at least one full-length, or near full-length element. In the case of sbo and Cornell samples, the only Hermes element sequences in the genome that contain priming sites for both PCR primers appear to be full-length elements. All other samples contain between 1 and 5 different-sized elements, with the Maryland strain exhibiting the greatest diversity. Variation in the size and number of internally deleted Hermes elements was also observed amongst individuals within some strains (data not shown). This pattern of size variation is similar to that observed for other active transposable element systems, including P, hobo, Tam3 and Ac (Berg & Howe, 1989). Unfortunately, the PCR band intensities cannot be correlated to element copy number due to preferential amplification of shorter PCR products and the non-linear nature of the PCR amplification conditions used in this experiment.

(iii) The Hermes transposase

Examination of the DNA sequence shown in FIG. 3 revealed the presence of a single long open reading frame (ORF1) that beings at nucleotide 450 and ends at 2285. Sequences resembling consensus eukaryotic TATA and CAAT sequences can be found around nucleotides 396 and 354 respectively and potential polyadenylation signals can be found within 100 bp of the end of ORF1. The locations of the putative CAAT and TATA sequences do not coincide with those proposed for the hobo element (Streck, Mac-Gaffey & Beckendorf, 1986; Calvi et al. 1991); however, a potential polyadenylation signal sequence is present exactly 14 bp beyond the end of ORF1 in both hobo and Hermes. Conceptual translation of ORF1 yields a protein sequence comprising 612 amino acids that displays 55% identity and 71% similarity to the hobo-transposase (FIG. 5). Thus ORF1 appears to encode part, if not all, of the Hermes transposase protein.

Comparisons of the Hermes sequence with those of Hobo, Ac, Tam3 and the Ac-like element from *P. glaucum* clearly show that the Hermes transposase protein sequence is most similar to that of hobo. In addition to the similarities reported by Calvi et al. (1991), Feldmar & Kunze (1991) and Hehl et al. (1991), we find that all five transposase proteins are indeed alignable over their entire length (data not shown).

Figures 6A, 6B:
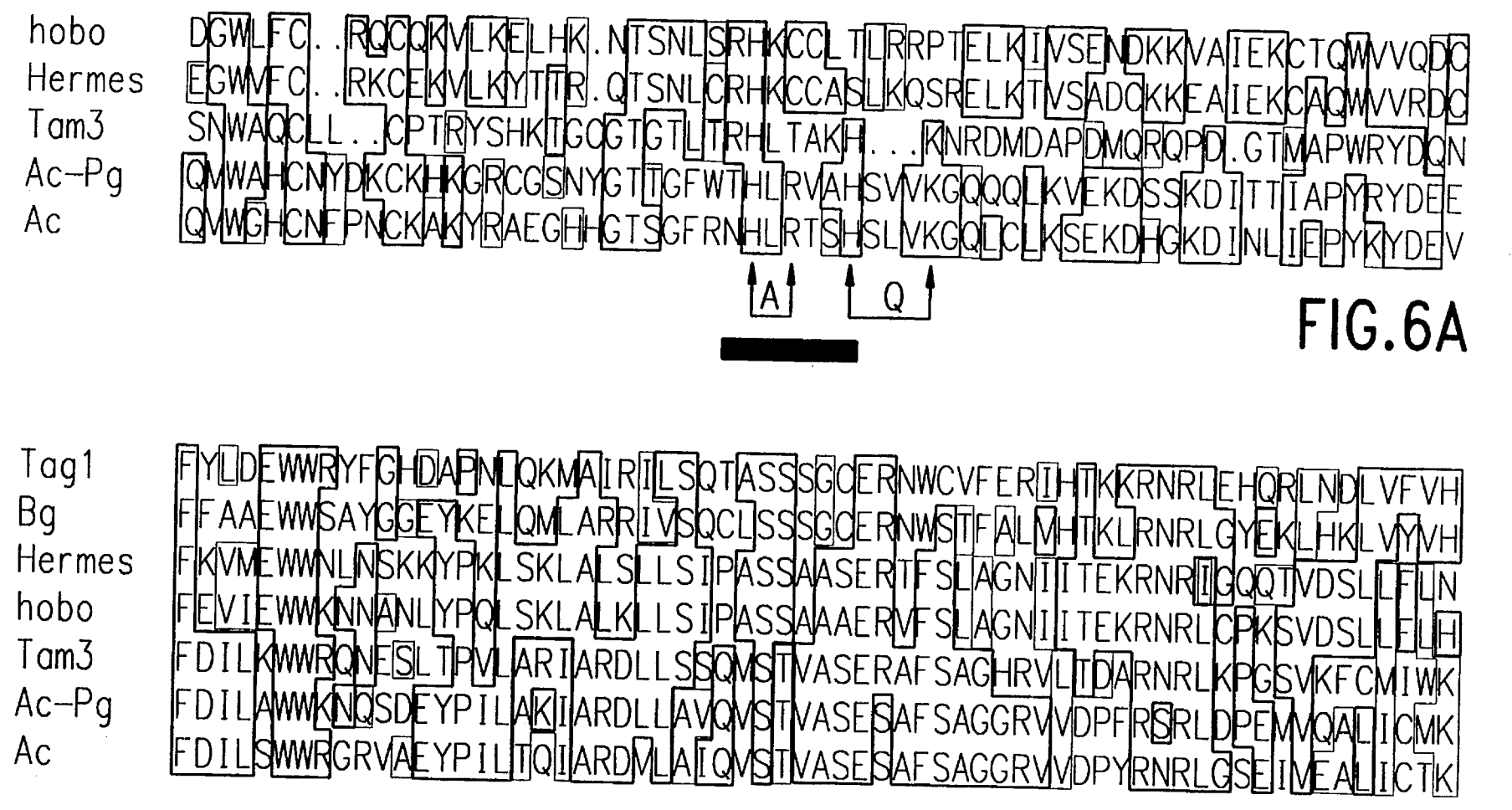

A histidine residue in this region, corresponding to His$^{191}$ known to be important for DNA binding, in the Ac transposase, is conserved in all five proteins. This suggests that this region in general, and the conserved histidine in particular, plays a crucial role in the DNA binding of all five transposases. The second region, shown in FIG. 6b, exhibits the highest levels of sequence conservation amongst all hAT element transposases and is located near their C-termini. When sequences from this region were used to search translations of the GenBank/EMBL/DDBJ nucleotide sequence databases, sequence similarity to two other transposable elements Tag1 from *Arabidopsis thaliana* (Tsay et al. 1993) and Bg from *Z. mays* (Hartings et al. 1991), was discovered. Further analysis of these elements showed that they share several other short regions of coding sequence similarity in various reading frames; however, in the absence of transcriptional information the significance of these other regions is uncertain.

(iv) Hermes terminal and subterminal sequences

Comparison of the left and right terminal sequences of Hermes reveals that they are composed of 17 bp imperfect inverted repeats (FIG. 2). The left terminal inverted repeat of Hermes differs from that of hobo by two bases, wile the right terminus of Hermes differs from the corresponding region of hobo by only a single nucleotide. When the inverted terminal sequences of other members of the hAT element family are aligned with those of Hermes, an interesting pattern emerges. Although several hAT elements have imperfect inverted repeats all share a conserved A and G at positions 2 and 5 respectively, in their left inverted terminal repeats and a complementary C and T in their right terminal sequences (FIG. 7). This A2G5 pattern is not universal to all short inverted repeat-type elements. Other elements that conform to this pattern (apart from the hAT family members discussed above), include the Ispr element from *Pisum sativum* (pea) (Bhattacharyya et al. 1990), Tpc1 from *Petroselinum crispum* (Parsley) (Herrmann, Schulz & Hahlbrock, 1988), 1723 from *Xenopus laevis* (Kay & David, 1983), and TECth1 from *Chironomus thummi* (Wobus et al. 1990). Interestingly, all these elements generate 8 bp target site duplications upon transposition. These observations suggest that the Ispr, Tpc1, 1723 and TECth1 elements may excise and transpose using an enzymology similar to that employed by hAT elements and may perhaps be evolutionarily related. In addition, the recombination signal sequences (RSS) required for DNA rearrangements of the V(D)J segments of vertebrate immunoglobin and T-cell receptor genes (Tonegawa, 1983; Hesse et al. 1989) also conform to this A2G5 pattern (FIG. 7).

With the exception of the inverted repeats, Hermes sequences outside of ORF1 show little similarity to those of hobo or any of the other members of the hAT element family. In the Ac element, substantially located AAACGG repeats are bound by the Ac transposase, yet similar repeated motifs are not found in Tam1, hobo or Hermes. The pentanucleotide GTGGC does appear within 20 bp of the left and right termini in both the hobo and Hermes sequences (FIG. 3) although the significance of this sequence has not been established.

hAT element inverted terminal repeats

A comparison of the terminal inverted repeats of Hermes with those of the other members of the hAT family, including the Bg and Tag1 elements, revealed a previously undocumented sequence similarity (FIG. 7). These elements, although having inverted repeats of various lengths and sequence compositions, all have an A at position 2 and a G at position 5 of their left termini, and complementary bases at the corresponding positions in their right termini. This observation suggests that these nucleotides play a central role in the biochemistry of recombination in this family of elements. A survey of the termini of other short inverted repeat-type elements revealed that several others, including Ispr, Tpc1, TECth1, and 1723 also follow this pattern. We feel that this A2G5 motif is unlikely to be fortuitous. All these elements share the common feature of generating an 8 bp insertion site duplication and, in the case where excision has been studied, cause the addition of supernumerary nucleotides that form short palindromes at the site rejoining (Pohlman, Fendorff & Messing, 1984; Coen, Carpenter & Martin, 1986; Atkinson, Warren & O'Brochta, 1993). The proposed mechanisms of breakage and rejoining following hAT element excision and the recombination of the variable (V), diversity (D) and joining (J) regions in lymphocytes are both thought to involve the formation and resolution of hairpin structures (Coen, Carpenter & Martin, 1986; Lieber, 191; Roth et al. 1992). Examination of the recombination signal sequence heptamer repeats that delimit the various V(D)J sequences removed during lymphoid cell development revealed that they also follow the A2G5 pattern. This similarity in the structure of the recombination reaction-products and the substrates for recombination suggest that V(D)J recombination and hAT element excision may share common enzymologies.

The above isolation and characterization of the Hermes element is set forth in detail in a document authored by the inventors published in August, 1994, Warren et al. The full contents of that publication are incorporated herein by reference.

Demonstration of Hermes' ability to transpose in Musca domestica

Methods

Transposition assay

We used the transposition assay developed by us and described elsewhere. Our only modification of this assay was to use a "donor plasmid" that contained a Hermes element instead of hobo sequences and a "helper" plasmid consisting of the Hermes transposase coding region under the regulatory control of the *D. melanogaster* hsp 70 promoter. Embryo injections, plasmid recovery and plasmid screening were done as described.

Plasmid Constructions pHermesIIKanR (donor plasmid). The 3.5kb HindIII-BamHI fragment from pIPCRBam-6A (our clone carrying the right end of Hermes$^2$) the 2 5kb HindIII-EcoR1 fragment from PIPCREco-IB (our clone carrying the left end of Hermes$^2$) and the pKF2 vector$^3$ cut with BamHI and EcoR1 were ligated together simultaneously to yield the plasmid pKFHermes. The 1.4 kb EcoR1-SphI fragment from pUC-Kan (our clone carrying the Kanamycin resistance gene from pACYC18$^4$)was ligated into the HindIII site of pKF-Hermes after all terminal unpaired nucleotides were removed This plasmid is pHermesKan$^R$, carrying Kan$^R$ and the left end of Hermes, was inserted into the HindIII site of pIPCRBam$^5$ (our clone carrying another copy of the right end of Hermes$^2$). this plasmid is pHermesIIKan$^R$ and is identical to pHermesKan$^R$but with a different right terminal repeat of Hermes and different sequences flanking the right end. The right terminal inverted repeats of Hermes in these two plasmids differ by one nucleotide.

pHSHH1.9 (Hermes helper plasmid). The open reading frame of Hermes was isolated by using PCR to amplify genomic DNA with primers 453 and 2363R. Primer 453F (SEQ ID NO:49) was 5'GAGTTTAAGCAGTAGTA-GAGATTAGATGC3'. Primer 2363R (SEQ ID NO:50) was 5'CTTAAATTTTTTCCAGTCC3'. The amplication product began at nucleotide 425 and ended at nucleotide 2381. The terminal unpaired nucleotides of the amplification products were removed, the 1.9 kb products were treated with kinase and inserted in the EcoRV site of pBCKS+(Stratagene®). This plasmid is pHH1.9. The long ORF of Hermes was excised from pHH1.9 by digestion with XhoI and SmaI. The ORF was inserted in the EcoRV and SalI sites of pHSREM2. This plasmid is pHSHH1.9.

After screening $10^6$ target plasmids (pUCSacRB[1]) we recovered two interplasmid transposition events. Transposition resulted in the movement of only sequences delimited by the inverted repeats of Hermes and resulted in an 8 bp duplication of the insertion site. These features are characteristic of transpositional recombination mediated by hAT elements.

Accordingly, Hermes can transpose when introduced into the embryonic cells of *M. domestica* and is a functional transposable element.

2. Demonstration of Hermes' ability to act as a germline transformation vector in an insect from the family Drosophilidae.

Methods

Transformation procedure. We constructed a plasmid containing the mini-white gene of *D. melanogaster* flanked by right and left terminal sequences of the Hermes element. We coinjected this plasmid (pHermes-2+) and the tranposase expressing helper plasmid, pHSHH1.9, into preblastoderm embryos of *D. melanogaster*. Injection of the vector and helper plasmids, and subsequent identification of transgenic G1 animals followed the established procedures currently used for *D. melanogaster*.

Plasmid Construction pBSHermes. The 1.5kb saII-PvuII fragment from pHermesIIKanR was inserted at the Xho! and SmaI sites of pHSREM2. This plasmid is pHermesL. The 2.4kb SalI-BamHI fragment from pIPCRBam5[2] was inserted at the SaiI and XbaI sites of pHermesL to create pBASHermes.

pHermesw+. The 3.6 kb EcoRI fragment from pTR1H containing the mini white gene was inserted into the EcoRI site of pBSHermes. PTR1H was a gift from Dr. Greg Gloor, University of Western Ontario, Canada. This plasmid is pHermes-w+.

Results

Three independent experiments resulted in the production of transgenic insects. An average of 32% of fertile G0 adults developing from injected embryos produced transgenic progeny. Comparable frequencies are seen using P elements. 88% of the G0 adults producing tragenic progeny had multiple insertions of Hermes in the germline. This was indicated by the presence of multiple eye phenotypes ranging from light orange to dark red. We confirmed the presence of multiple insertions by genetic mapping. 57% of the G0 progeny with integration of Hermes in the germline produced clusters of transgenic progeny caused by premeiotic insertion of Hermes. We defined a cluster as 10% or more of the progeny. In some flies almost the entire germline was transformed resulting in over 90% of the progeny with an integrated Hermes element.

We confirmed the presence of Hermes-specific oligonucleotide primers were used with genomic DNA isolated from G1 adults. Hermes sequences were detected in all progeny with pigmented eyes but never detected in non-transformed white-eyed siblings. Donor-plasmid sequences flanking Hermes were never detected in progeny with pigmented eyes, confirming that Hermes integrated into the Drosophila genome by transpositional recombination.

Accordingly, Hermes can transpose in *D. melanogaster* and act as an efficient germline transformation vector in this non-host species.

This invention has been described in terms of generic scope, and by specific example. Except where indicated, examples are non-limiting, and alternatives will occur to those of ordinary skill in the art without the exercise of inventive skill, and remain within the scope of the invention. In particular, terminal sequences for the transpositional vector other than those specifically identified herein maybe used, in variations and the variation of transposase gene may be similarly employed. Other promoters will occur to those of skill in the art. Additional variations remain within the scope of the invention, save as excluded by the recitation of the claims set forth below.

What is claimed is:

1. An isolated nucleotide sequence consisting of the nucleotide sequence set forth in FIG. 5 (SEQ ID NO:1).

2. A transposition vector, comprising a first terminal nucleotide sequence, a nucleotide sequence encoding a protein whose expression is sought, and a second terminal sequence, wherein said first terminal sequence comprises the 17 nucleotide sequence CAGAGAACAACAACAAG (SEQ ID NO:20) and said second terminal sequence comprises the 17 nucleotide sequence CTTGTTGAAGTTCTCTG (SEQ ID NO:21).

3. The transpositional vector of claim 2, wherein said first terminal nucleotide sequence further comprises, in sequence, from nucleotide 18 up to and including nucleotide 434 of FIG. 3 (SEQ ID NO:1), and said second terminal sequence further comprises, in sequence, from nucleotide 2732 to nucleotide 2287 of FIG. 3 (SEQ ID NO:1).

4. A method of recombining heterologous DNA in an insect or insect line host through transposition, comprising injecting the transposition vector of claim 2 in amounts effective to achieve transposition.

5. A method of recombining heterologous DNA in an insect or insect cell line embryo expression host, comprising injecting the transposition vector of claim 2 in said insect or embryo expression host in amounts effective to achieve transposition, together with a transposase helper plasmid comprising a promoter operably linked to DNA encoding a transposase enzyme comprising the amino acid sequence set forth in FIG. 3.

6. The method of claim 4, wherein said method further comprises injecting said insect or insect cell line host with a transposase helper plasmid comprising a promoter operably linked to DNA encoding a transposase enzyme comprising the amino acid sequence set forth in FIG. 3.

\* \* \* \* \*

UNITED STATES PATENT AND TRADEMARK OFFICE
CERTIFICATE OF CORRECTION

PATENT NO. : 5,614,398

DATED : March 25, 1997

INVENTOR(S): David O'Brochta, et al.

It is certified that an error appears in the above-identified patent and that said Letters Patent is hereby corrected as shown below:

Column 1, line 2 "NIH, 03-5-20014" should read --NIH, R01GM4810201--.

Signed and Sealed this

Twenty-seventh Day of March, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 2749 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 450..2285

( x i ) SEQUENCE DESCRIPTION: SEQ ID NO:1:

```
CAGAGAACAA    CAACAAGTGG    CTTATTTGA    TACTTATGCG    CCACTTGCTA    CTTATGAGTA         60
```

-continued

```
CAATTGTGCT TTGCCACTTG AACAAAAAAT TCATTGATTC ATCGACACTC GGGTATGTTT      120

TGTCGTGTCG TTCTGCGCAC TCAGTTAAAT TTTTTGTCTT ACTCTCTTGC TCTCAGCACA      180

TCAAGTGTTG TTACTTGTTG TTACTCAGTC GCCTGCCTTA TGCTTTTGGA GAGCGAAAGC      240

ACAACGATCA GAACGGAGAA GTAACAACTT GTTTTGCTAA CAAGTGGCTT ATGCACTTGA      300

GTGTGTTTTA CACATGTTTT TGAGTTTCAC AGCAAAATGT TCCGATTTGA GCACAATAAT      360

TTTACCGTTA TTTTGAGTTT TTTAGTTTTG AATAATAAAT GTGATTTACT GTTCATCCTC      420

AAAAGAGTTT AAGCAGTAGT AGAGATTAG ATG CAG AAA ATG GAC AAT TTG GAA        473
                                  Met Gln Lys Met Asp Asn Leu Glu
                                   1               5

GTG AAA GCA AAA ATC AAC CAA GGA TTA TAT AAA ATT ACT CCG CGA CAT        521
Val Lys Ala Lys Ile Asn Gln Gly Leu Tyr Lys Ile Thr Pro Arg His
     10              15                  20

AAA GGA ACA AGT TTT ATT TGG AAC GTT TTA GCG GAT ATA CAG AAA GAA        569
Lys Gly Thr Ser Phe Ile Trp Asn Val Leu Ala Asp Ile Gln Lys Glu
 25              30                  35                       40

GAC GAT ACA TTG GTG GAA GGG TGG GTG TTT TGC CGA AAA TGC GAA AAA        617
Asp Asp Thr Leu Val Glu Gly Trp Val Phe Cys Arg Lys Cys Glu Lys
                 45                  50                  55

GTT TTA AAA TAC ACA ACT AGG CAG ACA TCA AAC TTA TGT CGT CAT AAA        665
Val Leu Lys Tyr Thr Thr Arg Gln Thr Ser Asn Leu Cys Arg His Lys
             60                  65                  70

TGC TGT GCC TCT CTA AAG CAA TCC CGA GAA TTA AAA ACT GTT TCA GCT        713
Cys Cys Ala Ser Leu Lys Gln Ser Arg Glu Leu Lys Thr Val Ser Ala
         75                  80                  85

GAT TGC AAA AAG GAA GCA ATT GAA AAA TGT GCA CAA TGG GTG GTA CGA        761
Asp Cys Lys Lys Glu Ala Ile Glu Lys Cys Ala Gln Trp Val Val Arg
     90                  95                 100

GAT TGT CGG CCT TTT TCG GCC GTC TCT GGA TCC GGC TTT ATC GAT ATG        809
Asp Cys Arg Pro Phe Ser Ala Val Ser Gly Ser Gly Phe Ile Asp Met
105             110                 115                     120

ATA AAA TTT TTT ATT AAA GTT GGA GCC GAA TAT GGT GAA CAT GTC AAC        857
Ile Lys Phe Phe Ile Lys Val Gly Ala Glu Tyr Gly Glu His Val Asn
                125                 130                 135

GTT GAG GAA TTG TTA CCA AGT CCA ATA ACG CTA TCG AGA AAG GTA ACT        905
Val Glu Glu Leu Leu Pro Ser Pro Ile Thr Leu Ser Arg Lys Val Thr
            140                 145                 150

TCG GAT GCA AAA GAA AAA AAA GCT CTG ATT AGT CGA GAA ATT AAG TCT        953
Ser Asp Ala Lys Glu Lys Lys Ala Leu Ile Ser Arg Glu Ile Lys Ser
        155                 160                 165

GCT GTA GAG AAA GAT GGT GCA TCA GCA ACG ATA GAT TTG TGG ACC GAT       1001
Ala Val Glu Lys Asp Gly Ala Ser Ala Thr Ile Asp Leu Trp Thr Asp
    170                 175                 180

AAT TAT ATA AAA CGG AAT TTT TTG GGA GTA ACG TTA CAC TAC CAT GAA       1049
Asn Tyr Ile Lys Arg Asn Phe Leu Gly Val Thr Leu His Tyr His Glu
185                 190                 195                 200

AAC AAT GAA CTG CGA GAT CTA ATT TTA GGT TTA AAG TCC TTA GAT TTT       1097
Asn Asn Glu Leu Arg Asp Leu Ile Leu Gly Leu Lys Ser Leu Asp Phe
                205                 210                 215

GAA AGA TCC ACA GCA GAA AAT ATT TAT AAG AAG CTT AAA GCC ATT TTT       1145
Glu Arg Ser Thr Ala Glu Asn Ile Tyr Lys Lys Leu Lys Ala Ile Phe
            220                 225                 230

TTA CAA TTC AAC GTC GAA GAC TTG AGT AGT ATA AAA TTT GTG ACA GAT       1193
Leu Gln Phe Asn Val Glu Asp Leu Ser Ser Ile Lys Phe Val Thr Asp
        235                 240                 245

AGA GGA GCC AAT GTC GTA AAA TCA TTG GCA AAT AAT ATC AGA ATT AAC       1241
Arg Gly Ala Asn Val Val Lys Ser Leu Ala Asn Asn Ile Arg Ile Asn
    250                 255                 260
```

| | | | | | | | | | | | | | | | | |
|---|---|---|---|---|---|---|---|---|---|---|---|---|---|---|---|---|
| TGC | AGC | AGC | CAT | TTG | CTT | TCA | AAC | GTG | TTG | GAA | AAT | TCA | TTT | GAG | GAG | 1289 |
| Cys | Ser | Ser | His | Leu | Leu | Ser | Asn | Val | Leu | Glu | Asn | Ser | Phe | Glu | Glu | |
| 265 | | | | 270 | | | | | 275 | | | | | | 280 | |
| ACA | CCT | GAA | CTC | AAT | GTG | CCT | ATT | CTT | GCT | TGC | AAA | AAT | ATT | GTA | AAA | 1337 |
| Thr | Pro | Glu | Leu | Asn | Val | Pro | Ile | Leu | Ala | Cys | Lys | Asn | Ile | Val | Lys | |
| | | | | 285 | | | | | 290 | | | | | 295 | | |
| TAT | TTC | AAG | AAA | GCC | AAT | CTG | CAG | CAC | AGA | CTT | CGA | AGT | TCT | TTA | AAA | 1385 |
| Tyr | Phe | Lys | Lys | Ala | Asn | Leu | Gln | His | Arg | Leu | Arg | Ser | Ser | Leu | Lys | |
| | | | 300 | | | | | 305 | | | | | 310 | | | |
| AGT | GAG | TGC | CCT | ACA | CGG | TGG | AAT | TCC | ACA | TAC | ACG | ATG | CTT | CGA | TCT | 1433 |
| Ser | Glu | Cys | Pro | Thr | Arg | Trp | Asn | Ser | Thr | Tyr | Thr | Met | Leu | Arg | Ser | |
| | | 315 | | | | | 320 | | | | | 325 | | | | |
| ATT | CTC | GAC | AAC | TGG | GAA | AGC | GTG | ATT | CAA | ATA | TTA | AGT | GAG | GCG | GGA | 1481 |
| Ile | Leu | Asp | Asn | Trp | Glu | Ser | Val | Ile | Gln | Ile | Leu | Ser | Glu | Ala | Gly | |
| | 330 | | | | | 335 | | | | | 340 | | | | | |
| GAG | ACA | CAG | AGA | ATT | GTT | CAT | ATA | AAT | AAG | TCG | ATA | ATT | CAA | ACA | ATG | 1529 |
| Glu | Thr | Gln | Arg | Ile | Val | His | Ile | Asn | Lys | Ser | Ile | Ile | Gln | Thr | Met | |
| 345 | | | | | 350 | | | | | 355 | | | | | 360 | |
| GTC | AAC | ATC | CTC | GAT | GGG | TTT | GAA | AGA | ATT | TTT | AAA | GAA | TTA | CAA | ACA | 1577 |
| Val | Asn | Ile | Leu | Asp | Gly | Phe | Glu | Arg | Ile | Phe | Lys | Glu | Leu | Gln | Thr | |
| | | | | 365 | | | | | 370 | | | | | 375 | | |
| TGC | AGT | TCA | CCA | TCT | CTG | TGT | TTT | GTT | GTG | CCT | TCC | ATT | TTA | AAA | GTA | 1625 |
| Cys | Ser | Ser | Pro | Ser | Leu | Cys | Phe | Val | Val | Pro | Ser | Ile | Leu | Lys | Val | |
| | | | 380 | | | | | 385 | | | | | 390 | | | |
| AAA | GAA | ATA | TGT | TCA | CCT | GAC | GTT | GGC | GAC | GTT | GCA | GAT | ATA | GCA | AAA | 1673 |
| Lys | Glu | Ile | Cys | Ser | Pro | Asp | Val | Gly | Asp | Val | Ala | Asp | Ile | Ala | Lys | |
| | | 395 | | | | | 400 | | | | | 405 | | | | |
| TTG | AAA | GTG | AAC | ATT | ATA | AAA | AAT | GTA | AGA | ATA | ATA | TGG | GAA | GAA | AAT | 1721 |
| Leu | Lys | Val | Asn | Ile | Ile | Lys | Asn | Val | Arg | Ile | Ile | Trp | Glu | Glu | Asn | |
| | 410 | | | | | 415 | | | | | 420 | | | | | |
| TTA | AGC | ATA | TGG | CAC | TAC | ACA | GCA | TTT | TTT | TTC | TAT | CCG | CCC | GCC | TTG | 1769 |
| Leu | Ser | Ile | Trp | His | Tyr | Thr | Ala | Phe | Phe | Phe | Tyr | Pro | Pro | Ala | Leu | |
| 425 | | | | | 430 | | | | | 435 | | | | | 440 | |
| CAT | ATG | CAA | CAA | GAG | AAA | GTG | GCA | CAA | ATT | AAA | GAA | TTT | TGC | TTA | TCC | 1817 |
| His | Met | Gln | Gln | Glu | Lys | Val | Ala | Gln | Ile | Lys | Glu | Phe | Cys | Leu | Ser | |
| | | | | 445 | | | | | 450 | | | | | 455 | | |
| AAA | ATG | GAA | GAT | TTG | GAA | TTA | ATA | AAC | CGC | ATG | AGT | TCC | TTT | AAC | GAA | 1865 |
| Lys | Met | Glu | Asp | Leu | Glu | Leu | Ile | Asn | Arg | Met | Ser | Ser | Phe | Asn | Glu | |
| | | | 460 | | | | | 465 | | | | | 470 | | | |
| TTA | TCC | GCA | ACT | CAG | CTT | AAC | CAG | TCG | GAC | TCC | AAT | AGC | CAC | AAC | AGT | 1913 |
| Leu | Ser | Ala | Thr | Gln | Leu | Asn | Gln | Ser | Asp | Ser | Asn | Ser | His | Asn | Ser | |
| | | 475 | | | | | 480 | | | | | 485 | | | | |
| ATA | GAT | TTA | ACA | TCC | CAT | TCA | AAA | GAC | ATT | TCA | ACG | ACA | AGT | TTC | TTT | 1961 |
| Ile | Asp | Leu | Thr | Ser | His | Ser | Lys | Asp | Ile | Ser | Thr | Thr | Ser | Phe | Phe | |
| | 490 | | | | | 495 | | | | | 500 | | | | | |
| TTC | CCG | CAA | TTA | ACT | CAG | AAC | AAT | AGT | CGT | GAG | CCA | CCA | GTG | TGT | CCA | 2009 |
| Phe | Pro | Gln | Leu | Thr | Gln | Asn | Asn | Ser | Arg | Glu | Pro | Pro | Val | Cys | Pro | |
| 505 | | | | | 510 | | | | | 515 | | | | | 520 | |
| AGC | GAT | GAA | TTT | GAA | TTT | TAT | CGT | AAA | GAA | ATA | GTT | ATT | TTA | AGC | GAA | 2057 |
| Ser | Asp | Glu | Phe | Glu | Phe | Tyr | Arg | Lys | Glu | Ile | Val | Ile | Leu | Ser | Glu | |
| | | | | 525 | | | | | 530 | | | | | 535 | | |
| GAT | TTT | AAA | GTT | ATG | GAA | TGG | TGG | AAT | CTT | AAT | TCA | AAA | AAG | TAT | CCT | 2105 |
| Asp | Phe | Lys | Val | Met | Glu | Trp | Trp | Asn | Leu | Asn | Ser | Lys | Lys | Tyr | Pro | |
| | | | 540 | | | | | 545 | | | | | 550 | | | |
| AAA | CTA | TCT | AAA | CTG | GCT | TTG | TCG | TTA | TTA | TCA | ATA | CCT | GCA | AGT | AGC | 2153 |
| Lys | Leu | Ser | Lys | Leu | Ala | Leu | Ser | Leu | Leu | Ser | Ile | Pro | Ala | Ser | Ser | |
| | | 555 | | | | | 560 | | | | | 565 | | | | |
| GCT | GCA | TCG | GAA | AGG | ACA | TTT | TCC | CTA | GCT | GGA | AAT | ATA | ATA | ACT | GAA | 2201 |
| Ala | Ala | Ser | Glu | Arg | Thr | Phe | Ser | Leu | Ala | Gly | Asn | Ile | Ile | Thr | Glu | |
| | 570 | | | | | 575 | | | | | 580 | | | | | |

| | | | | | | | | | | | | | | | | |
|---|---|---|---|---|---|---|---|---|---|---|---|---|---|---|---|---|
|AAG|AGA|AAC|AGG|ATT|GGG|CAA|CAA|ACT|GTC|GAC|AGC|TTG|TTA|TTT|TTA|2249|
|Lys|Arg|Asn|Arg|Ile|Gly|Gln|Gln|Thr|Val|Asp|Ser|Leu|Leu|Phe|Leu| |
|585| | | |590| | | | |595| | | | |600| | |

| | | | | | | | | | | |
|---|---|---|---|---|---|---|---|---|---|---|
|AAT|TCC|TTT|TAC|AAA|AAT|TTT|TGT|AAA|TTA|GAT|ATA|TAATTACATT|2295|
|Asn|Ser|Phe|Tyr|Lys|Asn|Phe|Cys|Lys|Leu|Asp|Ile| | |
| | | | |605| | | | |610| | | |

| | | | | |
|---|---|---|---|---|
|TTTAAATAAA|AAGAATATTT|TTTATAAGTT|TGTTTGTTAA|AATAAAAAAA|AAAAATAAAT|2355|
|AAATTTTGGA|CTGGAAAAAA|TTTAAGTTTA|AAAGAAGCAT|TTTTCTTTTT|TTTTTAATA|2415|
|TACTTATGCT|CTTTTCCTAG|TCTTGTACAG|AATCATATGC|AATACTACAA|ACAATAGCAC|2475|
|ACACACACAA|CCCTCATGTT|CAATGAGTAT|ACAACACAAC|AAGAAGTGAG|TATAATTTGC|2535|
|CAATTGACAA|ATCGCACACG|TCCACTTGTG|AGTTTGTACA|CTTTTTACTC|TCTCATACTC|2595|
|TAGCGGTGAT|CTTAACATCA|AACAACTGTT|GTTGTTAAGT|TGTGAAAAAA|TACTCGTGTA|2655|
|TAAAAAAATA|CTTGCACTCA|AAAGGCTTGA|CACCCAAAAC|ACTTGTGCTT|ATCTATGTGG|2715|
|CTTACGTTTG|CCTGTGGCTT|GTTGAAGTTC|TCTG| | |2749|

( 2 ) INFORMATION FOR SEQ ID NO:2:

( i ) SEQUENCE CHARACTERISTICS:
        ( A ) LENGTH: 612 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Gln|Lys|Met|Asp|Asn|Leu|Glu|Val|Lys|Ala|Lys|Ile|Asn|Gln|Gly|
|1| | | |5| | | | |10| | | | |15| |
|Leu|Tyr|Lys|Ile|Thr|Pro|Arg|His|Lys|Gly|Thr|Ser|Phe|Ile|Trp|Asn|
| | | |20| | | | |25| | | | |30| | |
|Val|Leu|Ala|Asp|Ile|Gln|Lys|Glu|Asp|Thr|Leu|Val|Glu|Gly|Trp| |
| | | |35| | | | |40| | | | |45| | |
|Val|Phe|Cys|Arg|Lys|Cys|Glu|Lys|Val|Leu|Lys|Tyr|Thr|Thr|Arg|Gln|
| | |50| | | | |55| | | | |60| | | |
|Thr|Ser|Asn|Leu|Cys|Arg|His|Lys|Cys|Cys|Ala|Ser|Leu|Lys|Gln|Ser|
|65| | | | |70| | | | |75| | | | |80|
|Arg|Glu|Leu|Lys|Thr|Val|Ser|Ala|Asp|Cys|Lys|Lys|Glu|Ala|Ile|Glu|
| | | | |85| | | | |90| | | | |95| |
|Lys|Cys|Ala|Gln|Trp|Val|Val|Arg|Asp|Cys|Arg|Pro|Phe|Ser|Ala|Val|
| | | |100| | | | |105| | | | |110| | |
|Ser|Gly|Ser|Gly|Phe|Ile|Asp|Met|Ile|Lys|Phe|Phe|Ile|Lys|Val|Gly|
| | |115| | | | |120| | | | |125| | | |
|Ala|Glu|Tyr|Gly|Glu|His|Val|Asn|Val|Glu|Glu|Leu|Pro|Ser|Pro| |
| |130| | | | |135| | | | |140| | | | |
|Ile|Thr|Leu|Ser|Arg|Lys|Val|Thr|Ser|Asp|Ala|Lys|Glu|Lys|Lys|Ala|
|145| | | | |150| | | | |155| | | | |160|
|Leu|Ile|Ser|Arg|Glu|Ile|Lys|Ser|Ala|Val|Glu|Lys|Asp|Gly|Ala|Ser|
| | | | |165| | | | |170| | | | |175| |
|Ala|Thr|Ile|Asp|Leu|Trp|Thr|Asp|Asn|Tyr|Ile|Lys|Arg|Asn|Phe|Leu|
| | | |180| | | | |185| | | | |190| | |
|Gly|Val|Thr|Leu|His|Tyr|His|Glu|Asn|Asn|Glu|Leu|Arg|Asp|Leu|Ile|
| | |195| | | | |200| | | | |205| | | |
|Leu|Gly|Leu|Lys|Ser|Leu|Asp|Phe|Glu|Arg|Ser|Thr|Ala|Glu|Asn|Ile|
| |210| | | | |215| | | | |220| | | | |
|Tyr|Lys|Lys|Leu|Lys|Ala|Ile|Phe|Leu|Gln|Phe|Asn|Val|Glu|Asp|Leu|
|225| | | | |230| | | | |235| | | | |240|

```
Ser  Ser  Ile  Lys  Phe  Val  Thr  Asp  Arg  Gly  Ala  Asn  Val  Val  Lys  Ser
               245                     250                          255

Leu  Ala  Asn  Asn  Ile  Arg  Ile  Asn  Cys  Ser  Ser  His  Leu  Leu  Ser  Asn
               260                     265                     270

Val  Leu  Glu  Asn  Ser  Phe  Glu  Glu  Thr  Pro  Glu  Leu  Asn  Val  Pro  Ile
               275                     280                     285

Leu  Ala  Cys  Lys  Asn  Ile  Val  Lys  Tyr  Phe  Lys  Lys  Ala  Asn  Leu  Gln
          290                     295                     300

His  Arg  Leu  Arg  Ser  Ser  Leu  Lys  Ser  Glu  Cys  Pro  Thr  Arg  Trp  Asn
305                          310                     315                     320

Ser  Thr  Tyr  Thr  Met  Leu  Arg  Ser  Ile  Leu  Asp  Asn  Trp  Glu  Ser  Val
               325                     330                          335

Ile  Gln  Ile  Leu  Ser  Glu  Ala  Gly  Glu  Thr  Gln  Arg  Ile  Val  His  Ile
               340                     345                          350

Asn  Lys  Ser  Ile  Ile  Gln  Thr  Met  Val  Asn  Ile  Leu  Asp  Gly  Phe  Glu
          355                     360                     365

Arg  Ile  Phe  Lys  Glu  Leu  Gln  Thr  Cys  Ser  Ser  Pro  Ser  Leu  Cys  Phe
     370                     375                     380

Val  Val  Pro  Ser  Ile  Leu  Lys  Val  Lys  Glu  Ile  Cys  Ser  Pro  Asp  Val
385                          390                     395                     400

Gly  Asp  Val  Ala  Asp  Ile  Ala  Lys  Leu  Lys  Val  Asn  Ile  Ile  Lys  Asn
               405                     410                          415

Val  Arg  Ile  Ile  Trp  Glu  Glu  Asn  Leu  Ser  Ile  Trp  His  Tyr  Thr  Ala
               420                     425                     430

Phe  Phe  Phe  Tyr  Pro  Pro  Ala  Leu  His  Met  Gln  Gln  Glu  Lys  Val  Ala
          435                     440                     445

Gln  Ile  Lys  Glu  Phe  Cys  Leu  Ser  Lys  Met  Glu  Asp  Leu  Glu  Leu  Ile
     450                     455                     460

Asn  Arg  Met  Ser  Ser  Phe  Asn  Glu  Leu  Ser  Ala  Thr  Gln  Leu  Asn  Gln
465                          470                     475                     480

Ser  Asp  Ser  Asn  Ser  His  Asn  Ser  Ile  Asp  Leu  Thr  Ser  His  Ser  Lys
                    485                     490                     495

Asp  Ile  Ser  Thr  Thr  Ser  Phe  Phe  Phe  Pro  Gln  Leu  Thr  Gln  Asn  Asn
               500                     505                     510

Ser  Arg  Glu  Pro  Pro  Val  Cys  Pro  Ser  Asp  Glu  Phe  Glu  Phe  Tyr  Arg
          515                     520                     525

Lys  Glu  Ile  Val  Ile  Leu  Ser  Glu  Asp  Phe  Lys  Val  Met  Glu  Trp  Trp
          530                     535                     540

Asn  Leu  Asn  Ser  Lys  Lys  Tyr  Pro  Lys  Leu  Ser  Lys  Leu  Ala  Leu  Ser
545                          550                     555                     560

Leu  Leu  Ser  Ile  Pro  Ala  Ser  Ser  Ala  Ala  Ser  Glu  Arg  Thr  Phe  Ser
               565                     570                     575

Leu  Ala  Gly  Asn  Ile  Ile  Thr  Glu  Lys  Arg  Asn  Arg  Ile  Gly  Gln  Gln
               580                     585                     590

Thr  Val  Asp  Ser  Leu  Leu  Phe  Leu  Asn  Ser  Phe  Tyr  Lys  Asn  Phe  Cys
          595                     600                     605

Lys  Leu  Asp  Ile
          610
```

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: unknown (D) TOPOLOGY: unknown (ii) MOLECULE TYPE: DNA (genomic)

(xi) SEQUENCE DESCRIPTION: SEQ ID NO:3:

TAATACCAAC TGCAATGCAG TCTGTATCAG AGAACAACAA CAAG 44

(2) INFORMATION FOR SEQ ID NO:4:

(i) SEQUENCE CHARACTERISTICS:
(A) LENGTH: 44 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

AAAATGGATA ATACGGCTTA TCCGTACCAG AGAACAACAA CAAG 44

(2) INFORMATION FOR SEQ ID NO:5:

(i) SEQUENCE CHARACTERISTICS:
(A) LENGTH: 44 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:5:

CATACGTTCA GGTACCGAAC TGTGAACCAG AGAACAACAA CAAG 44

(2) INFORMATION FOR SEQ ID NO:6:

(i) SEQUENCE CHARACTERISTICS:
(A) LENGTH: 44 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:6:

CTTGTTGAAG TTCTCTGGTG GAGGGTATAA AAACACAGTT GAAA 44

(2) INFORMATION FOR SEQ ID NO:7:

(i) SEQUENCE CHARACTERISTICS:
(A) LENGTH: 44 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:7:

CTTGTTGAAG TTCTCTCAAA TGATATATAC TATATATCAT TTGA 44

(2) INFORMATION FOR SEQ ID NO:8:

(i) SEQUENCE CHARACTERISTICS:
(A) LENGTH: 61 amino acids
(B) TYPE: amino acid
(C) STRANDEDNESS: Not Relevant
(D) TOPOLOGY: unknown (ii) MOLECULE TYPE: peptide (xi) SEQUENCE DESCRIPTION: SEQ ID NO:8:

```
Asp Gly Trp Leu Phe Cys Arg Gln Cys Gln Lys Val Leu Lys Phe Leu
 1               5                  10                  15

His Lys Asn Thr Ser Asn Leu Ser Arg His Lys Cys Cys Leu Thr Leu
             20                  25                  30

Arg Arg Pro Thr Glu Leu Lys Ile Val Ser Glu Asn Asp Lys Lys Val
             35                  40                  45

Ala Ile Glu Lys Cys Ala Gln Trp Val Val Gln Gln Cys
         50                  55              60
```

( 2 ) INFORMATION FOR SEQ ID NO:9:

( i ) SEQUENCE CHARACTERISTICS:
        ( A ) LENGTH: 61 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:9:

```
Glu Gly Trp Val Phe Cys Arg Lys Cys Glu Lys Val Leu Lys Tyr Thr
 1               5                  10                  15

Thr Arg Gln Thr Ser Asn Leu Cys Arg His Lys Cys Cys Ala Ser Leu
             20                  25                  30

Lys Gln Ser Arg Glu Leu Lys Thr Val Ser Ala Asp Cys Lys Lys Glu
             35                  40                  45

Ala Ile Glu Lys Cys Ala Gln Trp Val Val Arg Gln Cys
         50                  55              60
```

( 2 ) INFORMATION FOR SEQ ID NO:10:

( i ) SEQUENCE CHARACTERISTICS:
        ( A ) LENGTH: 58 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:10:

```
Ser Asn Trp Ala Gln Cys Leu Leu Cys Pro Thr Arg Tyr Ser His Lys
 1               5                  10                  15

Thr Gly Cys Gly Thr Gly Thr Leu Thr Arg His Leu Thr Ala Lys His
             20                  25                  30

Lys Asn Arg Asp Met Asp Ala Pro Asp Met Gln Arg Gln Pro Asp Gly
             35                  40                  45

Thr Met Ala Pro Trp Arg Tyr Asp Gln Asn
         50                  55
```

( 2 ) INFORMATION FOR SEQ ID NO:11:

( i ) SEQUENCE CHARACTERISTICS:
        ( A ) LENGTH: 64 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:11:

```
Gln Met Trp Ala His Cys Asn Tyr Asp Lys Cys Lys His Lys Gly Arg
 1               5                  10                  15

Cys Gly Ser Asn Tyr Gly Thr Thr Gly Phe Trp Thr His Leu Arg Val
```

```
                      20                           25                            30
Ala  His  Ser  Val  Val  Lys  Gly  Gln  Gln  Gln  Leu  Lys  Val  Glu  Lys  Asp
               35                       40                        45

Xaa  Ser  Lys  Asp  Ile  Thr  Thr  Ile  Ala  Pro  Tyr  Arg  Tyr  Asp  Glu  Glu
          50                       55                        60
```

( 2 ) INFORMATION FOR SEQ ID NO:12:

( i ) SEQUENCE CHARACTERISTICS:
    ( A ) LENGTH: 64 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:12:

```
Gln  Val  Trp  Gly  His  Cys  Asn  Phe  Pro  Asn  Cys  Lys  Ala  Lys  Tyr  Arg
 1                    5                       10                        15

Ala  Glu  Gly  His  His  Gly  Thr  Ser  Gly  Phe  Arg  Asn  His  Leu  Arg  Thr
               20                       25                        30

Ser  His  Ser  Leu  Val  Lys  Gly  Gln  Leu  Cys  Leu  Lys  Ser  Glu  Lys  Asp
               35                       40                        45

Xaa  Gly  Lys  Asp  Ile  Asn  Leu  Ile  Glu  Pro  Tyr  Lys  Tyr  Asp  Glu  Val
          50                       55                        60
```

( 2 ) INFORMATION FOR SEQ ID NO:13:

( i ) SEQUENCE CHARACTERISTICS:
    ( A ) LENGTH: 64 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:13:

```
Phe  Tyr  Leu  Asp  Glu  Trp  Trp  Arg  Tyr  Phe  Gly  His  Gln  Ala  Pro  Asn
 1                    5                       10                        15

Leu  Gln  Lys  Met  Ala  Ile  Arg  Ile  Leu  Ser  Gln  Thr  Ala  Ser  Ser  Ser
               20                       25                        30

Gly  Cys  Glu  Arg  Asn  Trp  Cys  Val  Phe  Glu  Arg  Ile  His  Thr  Lys  Lys
               35                       40                        45

Arg  Asn  Arg  Leu  Glu  His  Asp  Arg  Xaa  Glu  Asp  Leu  Val  Phe  Val  His
          50                       55                        60
```

( 2 ) INFORMATION FOR SEQ ID NO:14:

( i ) SEQUENCE CHARACTERISTICS:
    ( A ) LENGTH: 64 amino acids
    ( B ) TYPE: amino acid
    ( C ) STRANDEDNESS: Not Relevant
    ( D ) TOPOLOGY: unknown ( i i ) MOLECULE TYPE: peptide ( x i ) SEQUENCE DESCRIPTION: SEQ ID NO:14:

```
Phe  Phe  Ala  Ala  Glu  Trp  Trp  Ser  Ala  Tyr  Gly  Gly  Glu  Tyr  Lys  Glu
 1                    5                       10                        15

Leu  Gln  Met  Leu  Ala  Arg  Arg  Ile  Val  Ser  Gln  Cys  Leu  Ser  Ser  Ser
               20                       25                        30

Gly  Cys  Glu  Arg  Asn  Trp  Ser  Ile  Phe  Ala  Leu  Val  His  Thr  Lys  Leu
               35                       40                        45
```

Arg Asn Arg Leu Gly Tyr Glu Lys Xaa His Lys Leu Val Tyr Val His
    50                      55                      60

( 2 ) INFORMATION FOR SEQ ID NO:15:

( i ) SEQUENCE CHARACTERISTICS:
        ( A ) LENGTH: 64 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:15:

Phe Lys Tyr Met Glu Trp Trp Asn Leu Asn Ser Lys Lys Tyr Pro Lys
 1               5                  10                      15

Leu Ser Lys Leu Ala Leu Ser Leu Leu Ser Ile Pro Ala Ser Ser Ala
            20                  25                  30

Ala Ser Glu Arg Thr Phe Ser Leu Ala Gly Asn Ile Ile Thr Glu Lys
        35                  40                  45

Arg Asn Arg Ile Gly Gln Gln Ile Val Asp Ser Leu Leu Phe Ile Asn
    50                      55                      60

( 2 ) INFORMATION FOR SEQ ID NO:16:

( i ) SEQUENCE CHARACTERISTICS:
        ( A ) LENGTH: 64 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:16:

Phe Glu Val Ile Glu Trp Trp Lys Asn Asn Ala Asn Leu Tyr Pro Gln
 1               5                  10                      15

Leu Ser Lys Leu Ala Leu Lys Leu Leu Ser Ile Pro Ala Ser Ser Ala
            20                  25                  30

Ala Ala Glu Arg Val Phe Ser Leu Ala Gly Asn Ile Ile Thr Glu Lys
        35                  40                  45

Arg Asn Arg Leu Cys Pro Lys Ser Val Asp Ser Leu Leu Phe Leu His
    50                      55                      60

( 2 ) INFORMATION FOR SEQ ID NO:17:

( i ) SEQUENCE CHARACTERISTICS:
        ( A ) LENGTH: 64 amino acids
        ( B ) TYPE: amino acid
        ( C ) STRANDEDNESS: Not Relevant
        ( D ) TOPOLOGY: unknown ( i i ) MOLECULE TYPE: peptide ( x i ) SEQUENCE DESCRIPTION: SEQ ID NO:17:

Phe Asp Ile Leu Lys Trp Trp Arg Gln Asn Glu Xaa Leu Thr Pro Val
 1               5                  10                      15

Leu Ala Arg Ile Ala Arg Asp Leu Leu Ser Ser Gln Met Ser Thr Val
            20                  25                  30

Ala Ser Glu Arg Ala Phe Ser Ala Gly His Arg Val Leu Thr Asp Ala
        35                  40                  45

Arg Asn Arg Leu Lys Pro Gly Ser Val Lys Phe Cys Xaa Ile Trp Lys
    50                      55                      60

( 2 ) INFORMATION FOR SEQ ID NO:18:

( i ) SEQUENCE CHARACTERISTICS:
  ( A ) LENGTH: 64 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:18:

| Phe | Asp | Ile | Leu | Ala | Trp | Trp | Lys | Asn | Gln | Ser | Asp | Glu | Tyr | Pro | Ile |
|---|---|---|---|---|---|---|---|---|---|---|---|---|---|---|---|
| 1 | | | | 5 | | | | | 10 | | | | | 15 | |

| Leu | Ala | Lys | Ile | Ala | Arg | Asp | Leu | Leu | Ala | Val | Gln | Val | Ser | Thr | Val |
|---|---|---|---|---|---|---|---|---|---|---|---|---|---|---|---|
| | | | | 20 | | | | | 25 | | | | | 30 | |

| Ala | Ser | Glu | Ser | Ala | Phe | Ser | Ala | Gly | Gly | Arg | Val | Val | Asp | Pro | Phe |
|---|---|---|---|---|---|---|---|---|---|---|---|---|---|---|---|
| | | | 35 | | | | | 40 | | | | | 45 | | |

| Arg | Ser | Arg | Leu | Asp | Pro | Glu | Met | Val | Gln | Xaa | Leu | Ile | Cys | Xaa | Lys |
|---|---|---|---|---|---|---|---|---|---|---|---|---|---|---|---|
| | 50 | | | | | 55 | | | | | | 60 | | | |

( 2 ) INFORMATION FOR SEQ ID NO:19:

( i ) SEQUENCE CHARACTERISTICS:
  ( A ) LENGTH: 64 amino acids
  ( B ) TYPE: amino acid
  ( C ) STRANDEDNESS: Not Relevant
  ( D ) TOPOLOGY: unknown ( i i ) MOLECULE TYPE: peptide ( x i ) SEQUENCE DESCRIPTION: SEQ ID NO:19:

| Phe | Asp | Ile | Leu | Ser | Trp | Trp | Arg | Gly | Arg | Val | Ala | Glu | Tyr | Pro | Ile |
|---|---|---|---|---|---|---|---|---|---|---|---|---|---|---|---|
| 1 | | | | 5 | | | | | 10 | | | | | 15 | |

| Leu | Thr | Gln | Ile | Ala | Arg | Asp | Val | Leu | Ala | Ile | Gln | Val | Ser | Xaa | Val |
|---|---|---|---|---|---|---|---|---|---|---|---|---|---|---|---|
| | | | | 20 | | | | | 25 | | | | | 30 | |

| Ala | Ser | Glu | Ser | Ala | Phe | Ser | Ala | Gly | Gly | Arg | Val | Val | Asp | Pro | Tyr |
|---|---|---|---|---|---|---|---|---|---|---|---|---|---|---|---|
| | | | 35 | | | | | 40 | | | | | 45 | | |

| Arg | Asn | Arg | Leu | Gly | Ser | Glu | Ile | Val | Glu | Xaa | Leu | Ile | Cys | Thr | Lys |
|---|---|---|---|---|---|---|---|---|---|---|---|---|---|---|---|
| | 50 | | | | | 55 | | | | | | 60 | | | |

( 2 ) INFORMATION FOR SEQ ID NO:20:

( i ) SEQUENCE CHARACTERISTICS:
  ( A ) LENGTH: 17 base pairs
  ( B ) TYPE: nucleic acid
  ( C ) STRANDEDNESS: unknown
  ( D ) TOPOLOGY: unknown ( i i ) MOLECULE TYPE: other nucleic acid ( x i ) SEQUENCE DESCRIPTION: SEQ ID NO:20:

CAGAGAACAA CAACAAG  17

( 2 ) INFORMATION FOR SEQ ID NO:21:

( i ) SEQUENCE CHARACTERISTICS:
  ( A ) LENGTH: 17 base pairs
  ( B ) TYPE: nucleic acid
  ( C ) STRANDEDNESS: unknown
  ( D ) TOPOLOGY: unknown ( i i ) MOLECULE TYPE: other nucleic acid ( x i ) SEQUENCE DESCRIPTION: SEQ ID NO:21:

CTTGTTGAAG TTCTCTG  17

( 2 ) INFORMATION FOR SEQ ID NO:22:

( i ) SEQUENCE CHARACTERISTICS:
    ( A ) LENGTH: 12 base pairs
    ( B ) TYPE: nucleic acid
    ( C ) STRANDEDNESS: unknown
    ( D ) TOPOLOGY: unknown ( i i ) MOLECULE TYPE: other nucleic acid ( x i ) SEQUENCE DESCRIPTION: SEQ ID NO:22:

CAGAGAACTG CA      12

( 2 ) INFORMATION FOR SEQ ID NO:23:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:23:

TGCAGTTCTC TG      12

( 2 ) INFORMATION FOR SEQ ID NO:24:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:24:

CAGGGATGAA A      11

( 2 ) INFORMATION FOR SEQ ID NO:25:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:25:

TTTCATCCCT A      11

( 2 ) INFORMATION FOR SEQ ID NO:26:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:26:

TAGGGATGAA A      11

( 2 ) INFORMATION FOR SEQ ID NO:27:

( i ) SEQUENCE CHARACTERISTICS:
        ( A ) LENGTH: 11 base pairs
        ( B ) TYPE: nucleic acid
        ( C ) STRANDEDNESS: unknown (D) TOPOLOGY: unknown (ii) MOLECULE TYPE: other nucleic acid (xi) SEQUENCE DESCRIPTION: SEQ ID NO:27:

TTTCATCCCT G  11

(2) INFORMATION FOR SEQ ID NO:28:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:28:

TAGAGATGAA A  11

(2) INFORMATION FOR SEQ ID NO:29:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:29:

TTTCATCCCT A  11

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:30:

TAAAGATGTG AA  12

(2) INFORMATION FOR SEQ ID NO:31:

(i) SEQUENCE CHARACTERISTICS:
        (A) LENGTH: 12 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:31:

TTCACATCTT TA  12

(2) INFORMATION FOR SEQ ID NO:32:

(i) SEQUENCE CHARACTERISTICS:
        (A) LENGTH: 12 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:32:

TAGGGGTGGC AA                                                                                                12

( 2 ) INFORMATION FOR SEQ ID NO:33:

( i ) SEQUENCE CHARACTERISTICS:
                ( A ) LENGTH: 12 base pairs
                ( B ) TYPE: nucleic acid
                ( C ) STRANDEDNESS: unknown
                ( D ) TOPOLOGY: unknown ( i i ) MOLECULE TYPE: other nucleic acid ( x i ) SEQUENCE DESCRIPTION: SEQ ID NO:33:

TTGCCACCCC TA                                                                                                12

( 2 ) INFORMATION FOR SEQ ID NO:34:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: unknown ( i i ) MOLECULE TYPE: other nucleic acid ( x i ) SEQUENCE DESCRIPTION: SEQ ID NO:34:

TAGGGTGTAA ATGAG                                                                                             15

( 2 ) INFORMATION FOR SEQ ID NO:35:

( i ) SEQUENCE CHARACTERISTICS:
                ( A ) LENGTH: 16 base pairs
                ( B ) TYPE: nucleic acid
                ( C ) STRANDEDNESS: unknown
                ( D ) TOPOLOGY: unknown ( i i ) MOLECULE TYPE: other nucleic acid ( x i ) SEQUENCE DESCRIPTION: SEQ ID NO:35:

CTCATTTACA GCCCTA                                                                                            16

( 2 ) INFORMATION FOR SEQ ID NO:36:

( i ) SEQUENCE CHARACTERISTICS:
                ( A ) LENGTH: 18 base pairs
                ( B ) TYPE: nucleic acid
                ( C ) STRANDEDNESS: unknown
                ( D ) TOPOLOGY: unknown ( i i ) MOLECULE TYPE: other nucleic acid ( x i ) SEQUENCE DESCRIPTION: SEQ ID NO:36:

TAGGGATGTA GCGAACGT                                                                                          18

( 2 ) INFORMATION FOR SEQ ID NO:37:

( i ) SEQUENCE CHARACTERISTICS:
                ( A ) LENGTH: 18 base pairs
                ( B ) TYPE: nucleic acid
                ( C ) STRANDEDNESS: unknown
                ( D ) TOPOLOGY: unknown ( i i ) MOLECULE TYPE: other nucleic acid ( x i ) SEQUENCE DESCRIPTION: SEQ ID NO:37:

ACGTTCGCGA CATCTCTA                                                                                          18

( 2 ) INFORMATION FOR SEQ ID NO:38:

(i) SEQUENCE CHARACTERISTICS:
    (A) LENGTH: 17 base pairs
    (B) TYPE: nucleic acid
    (C) STRANDEDNESS: unknown
    (D) TOPOLOGY: unknown (ii) MOLECULE TYPE: other nucleic acid (xi) SEQUENCE DESCRIPTION: SEQ ID NO:38:

CAGGGAAAAC TTTATCG     17

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:39:

GGATAGAGTA AACCCTG     17

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:40:

CAAGGCCATA GAACTCC     17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:41:

GGAGTTCTAT GGCCTTG     17

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: unknown
        (D) TOPOLOGY: unknown (ii) MOLECULE TYPE: other nucleic acid (xi) SEQUENCE DESCRIPTION: SEQ ID NO:42:

CAATGTTTTC ACGCCCGACC CG     22

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: unknown ( D ) TOPOLOGY: unknown ( i i ) MOLECULE TYPE: other nucleic acid ( x i ) SEQUENCE DESCRIPTION: SEQ ID NO:43:

CGGGTCGGGC GTGAAAACAT TG 22

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:44:

TTGTGTTACT CAGTCGC 17

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:45:

GTTTGATGTT AAGATCACC 19

( 2 ) INFORMATION FOR SEQ ID NO:46:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:46:

CTGTGGATCT TTCAAAATAA GG 22

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:47:

GAGACACCTG AACTCAATGT GC 22

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:48:

CGCAGTTCAT TGTTTTCATG G 21

( 2 ) INFORMATION FOR SEQ ID NO:49:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:49:

GAGTTTAAGC AGTAGTAGAG ATTAGATGC 29

( 2 ) INFORMATION FOR SEQ ID NO:50:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( i i ) MOLECULE TYPE: other nucleic acid ( x i ) SEQUENCE DESCRIPTION: SEQ ID NO:50:

CTTAAATTTT TTCCAGTCC 19